United States Patent
Wai et al.

[11] Patent Number: 5,780,480
[45] Date of Patent: Jul. 14, 1998

[54] FIBRINOGEN RECEPTOR ANTAGONISTS

[75] Inventors: John Wai, Harleysville; Thorsten E. Fisher, Hatfield; Mark E. Duggan, Schwenksville; George D. Hartman, Lansdale; James J. Perkins, Churchville, all of Pa.

[73] Assignee: Merck & Co., Inc., Rahway, N.J.

[21] Appl. No.: 807,843

[22] Filed: Feb. 26, 1997

Related U.S. Application Data

[60] Provisional application No. 60/012,380 Feb. 28, 1996.

[51] Int. Cl.$^6$ .................. A01N 43/42; C07D 471/00; C07D 211/32
[52] U.S. Cl. .................. 514/292; 514/309; 514/318; 546/84; 546/87; 546/141; 546/194; 546/234; 546/235; 546/236
[58] Field of Search .................. 546/194, 141, 546/236, 84, 87, 234, 235; 514/309, 292, 318

[56] References Cited

U.S. PATENT DOCUMENTS

| | | | |
|---|---|---|---|
| 4,064,255 | 12/1977 | Champseix et al. | 424/267 |
| 4,122,255 | 10/1978 | Krapcho | 542/421 |
| 4,243,807 | 1/1981 | Friebe et al. | 546/232 |
| 4,622,331 | 11/1986 | Jozic | 514/331 |
| 4,760,064 | 7/1988 | Tominaga et al. | 514/253 |
| 5,008,274 | 4/1991 | Nishi et al. | 514/312 |
| 5,030,654 | 7/1991 | Barnish et al. | 514/510 |
| 5,064,814 | 11/1991 | Klein et al. | 514/18 |
| 5,071,853 | 12/1991 | Bigge et al. | 514/290 |
| 5,183,810 | 2/1993 | Greenlee et al. | 514/63 |
| 5,206,373 | 4/1993 | Chung et al. | 546/335 |
| 5,227,490 | 7/1993 | Hartman et al. | 514/317 |
| 5,260,307 | 11/1993 | Ackermann et al. | 514/323 |
| 5,393,760 | 2/1995 | Ackermann et al. | 514/323 |
| 5,464,833 | 11/1995 | Nakai et al. | 514/251 |
| 5,532,232 | 7/1996 | Ackermann et al. | 514/183 |
| 5,556,977 | 9/1996 | Wayne et al. | 544/360 |
| 5,578,594 | 11/1996 | Ackermann et al. | 514/236.2 |
| 5,583,133 | 12/1996 | Ackermann et al. | 514/183 |
| 5,595,999 | 1/1997 | Ackermann et al. | 514/309 |

FOREIGN PATENT DOCUMENTS

| | | |
|---|---|---|
| 0 352 249 | 1/1990 | European Pat. Off. |
| 0 372 486 | 6/1990 | European Pat. Off. |
| 0 381 033 | 8/1990 | European Pat. Off. |
| 0 384 362 | 8/1990 | European Pat. Off. |
| 0 405 537 | 1/1991 | European Pat. Off. |
| 0 478 328 | 4/1992 | European Pat. Off. |
| 0 478 362 | 4/1992 | European Pat. Off. |
| 0 478 363 | 4/1992 | European Pat. Off. |
| 0 479 481 | 4/1992 | European Pat. Off. |
| 94/08962 | 4/1994 | WIPO |

OTHER PUBLICATIONS

Ford–Hutchinson et al., Can. J. Physiol. Pharmacol., "The Pharmacology of L–760,596, a potent and selective thromboxane ...", vol. 67, pp. 989–993 (1989).

Deruiter et. al., "N–and 2–Substituted N–(Phenylsulfonyl) Glycines as Inhibitors ...", J. Med. Chem., 1989, vol. 32, pp. 145–151.

*Primary Examiner*—Mukund J. Shah
*Assistant Examiner*—Tamthom T. Ngo
*Attorney, Agent, or Firm*—Richard S. Parr; Mel Winokur; Carol S. Quagliato

[57] ABSTRACT

Fibrinogen receptor antagonists of the general formula:

$$X\text{-}A\text{-}Y\text{-}Z\text{-}B \qquad \text{I}$$

and which includes, for example, the compounds of formula

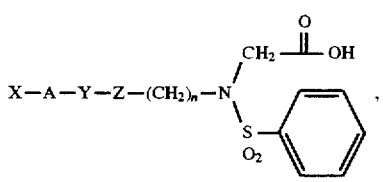

are useful for inhibiting the binding of fibrinogen to blood platelets, inhibiting the aggregation of blood platelets, treating thrombus formation or embolus formation, and preventing thrombus or embolus formation.

11 Claims, No Drawings

FIBRINOGEN RECEPTOR ANTAGONISTS

CROSS-REFERENCE TO RELATED APPLICATIONS

This application claims priority to U.S. provisional application No. 60/012,380, filed Feb. 28, 1996.

BACKGROUND OF THE INVENTION

The invention relates generally to modulating cell adhesion and to inhibiting the binding of fibrinogen and other proteins to blood platelets, and inhibiting the aggregation of blood platelets specifically to the gp IIb/IIIa fibrinogen receptor site. Fibrinogen is a glycoprotein present in blood plasma that participates in platelet aggregation and in fibrin formation. Platelets are cell-like anucleated fragments, found in the blood of all mammals, that also participate in blood coagulation. Interaction of fibrinogen with the IIb/IIIa receptor site is known to be essential for normal platelet function.

When a blood vessel is damaged by an injury or other causative factor, platelets adhere to the disrupted subendothethial surface. The adherent platelets subsequently release biologically active constituents and aggregate. Aggregation is initiated by the binding of agonists, such as thrombin, epinephrine, or ADP to specific platelet membrane receptors. Stimulation by agonists results in exposure of latent fibrinogen receptors on the platelet surface, and binding of fibrinogen to the glycoprotein IIb/IIIa receptor complex.

Attempts have been made to use natural products and synthetic peptides to determine the mechanism of adhesion and platelet aggregation. For example, Rouslahti and Pierschbacher in *Science*, 238, 491–497 (1987), describe adhesive proteins such as fibronectin, vitronectin, osteopontin, collagens, thrombospondin, fibrinogen, and von Willebrand factor that are present in extracellular matrices and in blood. The proteins contain the tripeptide arginine-glycine-aspartic acid (RGD) as their glycoprotein IIb/IIIa recognition site. These arginine-glycine-aspartic acid containing tripeptides are recognized by at least one member of a family of structurally related receptors, integrins, which are heterodimeric proteins with two membrane-spanning subunits. The authors state that the conformation of the tripeptide sequence in the individual proteins may be critical to recognition specificity.

Cheresh in *Proc. Nat'l Acad. Sci. U.S.A.*, 84, 6471–6475, (1987), describes an Arg-Gly-Asp directed adhesion receptor expressed by human endothethial cells that is structurally similar to the IIb/IIIa complex on platelets but is antigenically and functionally distinct. This receptor is directly involved in endothelial cell attachment to fibrinogen, von Willebrand factor, and vitronectin.

Pierschbacher and Rouslahti, in *J. of Biol. Chem.*, 262, (36), 17294–17298 (1987) hypothesized that the Arg-Gly-Asp sequence alone would be a sufficient signal for receptor recognition and binding and that, therefore, the conformation of the tri-peptide sequence would be determinative. Various synthetic peptides were produced and the authors concluded that the sterochemical conformation of Arg-Gly-Asp as influenced by enantiomeric substitutions or additions to this sequence significantly influenced receptor-ligand interaction. The authors further showed that cyclization of a decapeptide by forming a disulfide bridge between non-terminal residues Pen and Cys, rendered the peptide much less effective at inhibiting attachment to fibronectin.

In *Proc. Nat'l Acad. Sci. U.S.A.*, 81, 5985–5988 (1984), the same authors describe tetrapeptide variants of the cell recognition site of fibronectin that retain attachment-promoting activity. Peptides having a tetrapeptide recognition site are described in U.S. Pat. Nos. 4,589,881 and 4,614,517. A number of large polypeptide fragments in the cell-binding domain of fibronectin have cell-attachment activity. For example, see U.S. Pat. Nos. 4,517,686, 4,661, 111 and U.S. Pat. No. 4,578,079.

Ruggeri et al., *Proc. Nat'l Acad. Sci. U.S.A.*, 83, 5708–5712 (1986) explore a series of synthetic peptides designed in lengths to 16 residues, that contain RGD and a valine attached to the aspartic acid residue of RGD that inhibit fibrinogen binding to platelets. See also Koczewiak et al., *Biochem.* 23, 1767–1774 (1984); Ginsberg et al., *J. Biol. Chem.* 260(7), 3931–3936 (1985); and Haverstick et al., *Blood* 66(4), 946–952 (1985). Other inhibitors are disclosed in Eur. Pat. App. Nos. 275,748 and 298,820.

A number of low molecular weight polypeptide factors have been isolated from snake venom. These factors apparently have high affinity for the gp IIb/IIIa complex. For example, Huang et al., *J. Biol Chem.*, 262, 16157–16163 (1987); Huang et al., *Biochemistry*, 28, 661–666 (1989) describe the primary structure of the venom trigramin which is a 72 amino acid polypeptide that contains the RGD subunit. Echistatin is another compound which has high affinity for the gp IIb/IIIa complex. This polypeptide contains 49 amino acids and has the RGD subunit and various disulfide bridges. Gan et al., *J. Biol. Chem.*, 263, 19827–19832 (1988). See also, Dennis et al., *Proc. Nat'l Acad. Sci. USA*, 87, 2471–2475 (1989). However, these snake venom factors also have high affinity for other members of the adhesive protein receptor family including the vitronectin and fibronectin receptors so are not selective for the gp IIb/IIIa complex.

While it is known that the tripeptide sequence Arg-Gly-Asp is present in certain polypeptides that can duplicate or inhibit the cell attachment-promoting effects of fibronectin and vitronectin, the tripeptide Arg-Gly-Asp has low activity. At present, there is little understanding of how other amino acids coupled to this sequence influence binding specificity. U.S. Pat. No 5,023,233 discloses small cyclic hexapeptides which contain the sequence Arg-Gly-Asp and are useful platelet aggregation inhibitors. U.S. Pat. No. 5,037,808 discloses the use of indolyl platelet-aggregation inhibitors which are believed to act by antagonizing interactions between fibrinogen and/or extracellular matrix proteins and the platelet gp IIb/IIIa receptor. U.S. Pat. No. 5,037,808 discloses guanidino peptide mimetic compounds that retain an Asp residue which inhibit platelet aggregation. WO9014103 describes the use of antibody-poly-peptide conjugates wherein said polypeptides contain the Arg-Gly-Asp (RGD) sequence.

WO9111458 discloses the use of large cyclic peptides containing RGD flanked by proline residues which are platelet aggregation inhibitors. WO9101331 discloses small cyclic platelet aggregation inhibitors which are synthetic cyclic pentapeptides containing the tripeptide sequence Arg-Gly-Asp and a thioether linkage in the cycle. U.S. Pat. No. 5,051,405 also discloses the use of peptides and pseudopeptides such as N-amidino-piperidine-3-carboxylglycyl-L-aspartyl-L-valine that inhibit platelet aggregation and thrombus formation in mammalian blood. EP 445 796 discloses linear compounds which can include internal piperazinyl or piperidinyl derivatives. EP437 367 discloses linear polypeptide fibrinogen receptor antagonists. U.S. Pat. No. 5,256,812 discloses compounds of the $R^1$-A-$(W)_a$-X-$(CH_2)_b$-$(Y)_c$-B-Z-COOR wherein $R^1$ is a guandidino or amidino moiety and A and B are chosen from specific monosubstituted aryl or heterocyclic moieties.

While a multitude of compounds or peptide analogs believed to inhibit platelet aggregation by inhibiting binding to a blood platelet by fibrinogen are known, the present invention provides novel fibrinogen receptor antagonists that have significant binding activity and are, therefore, useful for the reasons stated herein. A number of very serious diseases and disorders involve hyperthrombotic complications which lead to intravascular thrombi and emboli. Myocardial infarction, stroke, phlebitis and a number of other serious conditions create the need for novel and effective fibrinogen receptor antagonists.

SUMMARY OF THE INVENTION

One object of this invention is to provide novel compounds which are active as fibrinogen receptor antagonists. Fibrinogen receptor antagonists of this invention have the general formula:

X-A-Y-Z-B      I, and include, for example, the compounds of formula

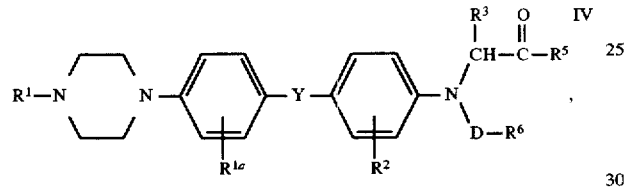

wherein the variable groups are defined in detail below.

Compounds of the invention are useful for inhibiting the binding of fibrinogen to blood platelets and for inhibiting the aggregation of blood platelets. Therefore, it is another object of this invention to provide methods of inhibiting the binding of fibrinogen to blood platelets, inhibiting the aggregation of blood platelets, treating thrombus formation or embolus formation, or preventing thrombus or embolus formation in a mammal, preferably a human, using the instant compounds. Combination therapies are also described which employ the instant compounds with other active agents such as a thrombolytic agent, an anticoagulant agent, and/or an antiplatelet agent. A further object of this invention is to provide pharmaceutical compositions which are useful in the above-described methods. Further objects of this invention will be apparent from the disclosure herein.

DETAILED DESCRIPTION OF THE INVENTION

The present invention provides compounds having the formula I

X-A-Y-Z-B      I and the pharmaceutically acceptable salts, esters, solvates and stereoisomers thereof wherein:
X is heterocycle;
heterocycle is selected from:
(1) a five or six membered saturated, partially unsaturated or aromatic ring which consists of carbon atoms and one, two or three heteroatoms selected from the group —O—, —N—, —N($R^1$)— and —S—, wherein one of the carbon atoms may be substituted with a member selected from $R^{1a}$ and —$NHR^1$,
(2) an eight to ten membered bicyclic ring system which is saturated, or completely or partially unsaturated, and which consists of carbon atoms and one, two or three heteroatoms selected from the group —O—, —N—, —N($R^1$)— and —S—, wherein one of the carbon atoms may be substituted with a member selected from $R^{1a}$ and —$NHR^1$,
(3) a thirteen to fourteen membered tricyclic ring system which is saturated, or completely or partially unsaturated, and which consists of carbon atoms and one, two or three heteroatoms selected from the group —O—, —N—, —N($R^1$)— and —S—, wherein one of the carbon atoms may be substituted with a member selected from $R^{1a}$ and —$NHR^1$;

A is a bond between X and Y or is selected from:
(1) phenyl substituted with $R^{1a}$,
(2) —N($R^1$)—, and (3) 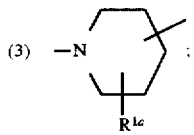

Y is selected from:
(1) —$C_{1-8}$ alkyl-,
(2) —$C_{4-10}$ cycloalkyl-,
(3) —$C_{0-8}$ alkyl-$NR^1$—CO—$C_{0-8}$ alkyl-,
(4) —$C_{0-8}$ alkyl-$CONR^1$—$C_{0-8}$ alkyl-,
(5) —$C_{0-8}$ alkyl-O—$C_{0-8}$ alkyl-,
(6) —$C_{0-8}$ alkyl-$SO_p$—$C_{0-8}$ alkyl-,
(7) —$(CH_2)_{0-8}$-aryl-$(CH_2)_{0-8}$-,
(8) (—$CH_2)_{0-6}$-aryl-$SO_p$-,
(9) —$(CH_2)_{0-8}$-aryl-CO—$(CH_2)_{0-8}$-,
(10) —$(CH_2)_{0-6}$-aryl-$SO_p$—$(CH_2)_{0-6}$-,
(11) —$(CH_2)_{0-6}$-$NR^1$—$(CH_2)_{0-6}$-,
(12) —$(CH_2)_{0-6}$-aryl-CH(OH)—$(CH_2)_{0-6}$-,
(13) —$(CH_2)_{0-8}$-aryl-CONH—$(CH_2)_{0-8}$-,
(14) —$C_{0-8}$ alkyl-$SO_p$—$NR^1$-$C_{0-8}$ alkyl-,
(15) —$C_{0-8}$ alkyl-CO—$C_{0-8}$ alkyl-, and
(16) —$C_{0-8}$ alkyl-CH(OH)—$C_{0-8}$-alkyl-;
p is an integer selected from 0, 1 and 2;
Z is selected from aryl and heterocycle;
aryl is a 5- or 6-membered aromatic ring system which is unsubstituted or mono-, di- or tri-substituted with $R^2$;
B is

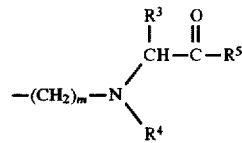

wherein m is an integer selected from 0 and 1;
$R^1$ and $R^3$ are independently selected at each occurrence from:
(1) hydrogen,
(2) $C_{1-10}$ alkyl-,
(3) $C_{3-8}$ cycloalkyl-,
(4) aryl-$C_{0-8}$ alkyl-,
(5) amino-$C_{0-8}$ alkyl-,
(6) $C_{1-6}$ alkylamino-$C_{0-8}$ alkyl-,
(7) $C_{1-6}$ dialkylamino-$C_{0-8}$ alkyl-, (8) $C_{1-3}$ acylamino-$C_{0-8}$ alkyl-, (9) $C_{1-4}$ alkoxy-$C_{0-6}$ alkyl-,

(10) —$C_{0-6}$ alkyl-$CO_2H$,

(11) —$C_{0-6}$ alkyl-$CO_2C_{1-3}$ alkyl,

(12) —O—$C_{0-6}$ alkyl-$CO_2H$ and

(13) hydroxy-$C_{0-6}$ alkyl-;

$R^{1a}$ is independently selected at each occurrence from:

(1) hydrogen, (2) halogen, (3) $C_{1-10}$ alkyl-, (4) $C_{3-8}$ cycloalkyl-, (5) aryl-$C_{0-8}$ alkyl-, (6) amino-$C_{0-8}$ alkyl-, (7) $C_{1-6}$ alkylamino-$C_{0-8}$ alkyl-, (8) $C_{1-6}$ dialkylamino-$C_{0-8}$ alkyl-, (9) $C_{1-3}$ acylamino-$C_{0-8}$ alkyl-,

(10) $C_{1-4}$ alkoxy-$C_{0-6}$ alkyl-,

(11) —$C_{0-6}$ alkyl-$CO_2H$,

(12) —$C_{0-6}$ alkyl-$CO_2C_{1-3}$ alkyl,

(13) —O—$C_{0-6}$ alkyl-$CO_2H$,

(14) hydroxy $C_{0-6}$ alkyl and

(15) oxo (=O);

$R^2$ is independently selected at each occurrence from:

(1) hydrogen, (2) halogen, (3) $C_{1-10}$ alkyl-, (4) $C_{3-8}$ cycloalkyl-, (5) aryl-$C_{0-8}$ alkyl-, (6) amino-$C_{0-8}$ alkyl-, (7) $C_{1-6}$ alkylamino-$C_{0-8}$ alkyl-, (8) $C_{1-6}$ dialkylamino-$C_{0-8}$ alkyl-, (9) $C_{1-3}$ acylamino-$C_{0-8}$ alkyl-,

(10) $C_{1-4}$ alkoxy-$C_{0-6}$ alkyl-,

(11) —$C_{0-6}$ alkyl-$CO_2H$,

(12) —$C_{0-6}$ alkyl-$CO_2C_{1-3}$ alkyl,

(13) —O—$C_{0-6}$ alkyl-$CO_2H$, and

(14) hydroxy $C_{0-6}$ alkyl;

$R^4$ is selected from (1) —$(CH_2)_p$-D-$R^6$ wherein p is defined above,

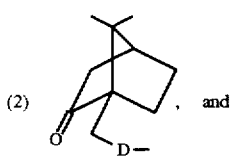

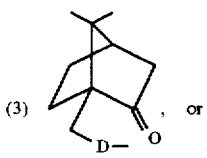

(4) when Z is unsubstituted or substituted phenyl and m is zero, $R^4$ together with the nitrogen to which it is attached can form a bicyclic structure with Z (phenyl) as follows:

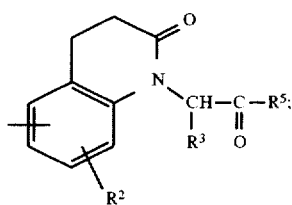

D is selected from —$SO_2$— and —C(O)—;

$R^5$ is selected from:

(1) —OH, (2) $C_{1-8}$ alkyloxy-, (3) aryl $C_{0-6}$ alkyloxy-, (4) $C_{1-8}$ alkylcarbonyloxy $C_{1-4}$ alkyloxy-, (5) aryl $C_{1-8}$ alkylcarbonyloxy $C_{1-4}$ alkyloxy-, and (6) L- or D-amino acid joined by an amide linkage and wherein the carboxylic acid moiety of said amino acid is as the free acid or is esterified by $C_{1-6}$ alkyl; and $R^6$ is selected from:

(1) —$C_{1-6}$alkyl, unsusbstituted, mono- or di-substituted with $R^{1a}$, (2) —($C_{0-6}$alkyl)aryl, wherein the alkyl group is unsusbstituted, mono- or di-substituted with $R^{1a}$, (3) —($C_{0-6}$alkyl)heterocycle, wherein the alkyl group is unsusbstituted, mono- or di-substituted with $R^{1a}$, (4) —$NR^1(C_{1-6}$alkyl), wherein the alkyl group is unsusbstituted, mono- or di-substituted with $R^{1a}$, (5) —$NR^1(C_{0-6}$alkylaryl), wherein the alkyl group is unsusbstituted, mono- or di-substituted with $R^{1a}$, (6) —$NR^1(C_{0-6}$alkylheterocycle), wherein the alkyl group is unsusbstituted, mono- or di-substituted with $R^{1a}$, (7) —$C_{3-6}$ cycloalkyl, and (8) —$CF_3$.

In a one embodiment of this invention are compounds of formula I which have the particular formula II:

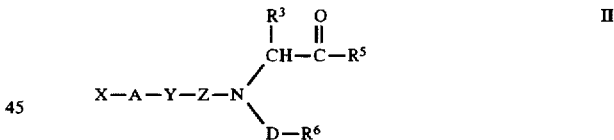

and the pharmaceutically acceptable salts, solvates and stereoisomers thereof wherein:

X-A- together represent a group selected from:

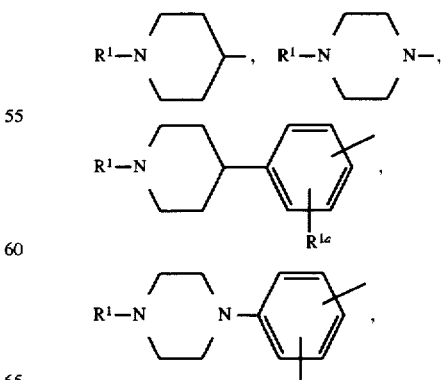

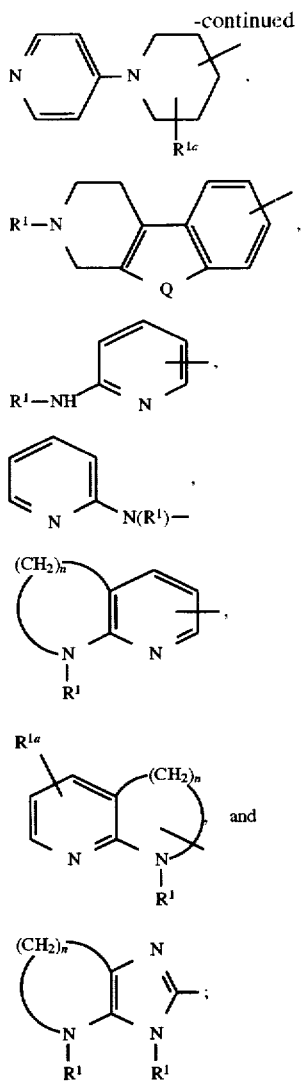

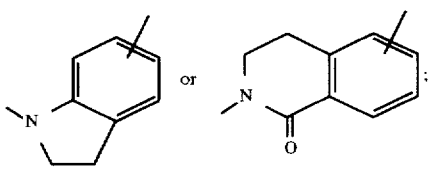

n is an integer selected from 2, 3, 4, and 5;
Q is selected from —N(R$^1$)—, —S— and —O—;
Y is selected from:

(1) —C$_{0-8}$ alkyl-NR$^1$-CO-C$_{0-8}$ alkyl-,
(2) —C$_{0-8}$ alkyl-CONR$^1$-C$_{0-8}$ alkyl-,
(3) —C$_{0-8}$ alkyl-O-C$_{0-8}$ alkyl-,
(4) —C$_{0-8}$ alkyl-SO$_p$-C$_{0-8}$ alkyl-,
(5) —(CH$_2$)$_{0-6}$-NR$^1$-(CH$_2$)$_{0-6}$-,
(6) —C$_{0-8}$ alkyl-SO$_p$-NR$^1$-C$_{0-8}$ alkyl-,
(7) —C$_{0-8}$ alkyl-CO-C$_{0-8}$ alkyl-, and
(8) —C$_{0-8}$ alkyl-CH(OH)-C$_{0-8}$-alkyl-;

p is an integer selected from 0, 1 and 2;
Z is selected from (1) aryl and
(2) a five or six membered saturated, partially unsaturated or aromatic heterocyclic ring which is unsubstituted, or monosubstituted or disubstituted with R$^{1a}$, which consists of carbon atoms and one, two or three heteroatoms selected from the group —O—, —N—, —N(R$^1$)— and —S—, and which may be fused to a benzene ring to form a bicyclic structure, for example, aryl is a 5- or 6-membered aromatic carbon ring which is unsubstituted or mono-, di- or tri-substituted with R$^2$;

R$^1$ is independently selected at each occurrence from —H, C$_{1-10}$ alkyl, C$_{3-8}$ cycloalkyl-, aryl-C$_{0-8}$ alkyl- and hydroxy-C$_{0-6}$ alkyl-;

R$^{1a}$ is independently selected at each occurrence from —H, halogen, —C$_{1-10}$ alkyl, C$_{3-8}$ cycloalkyl-, aryl-C$_{0-8}$ alkyl-, and amino-C$_{0-8}$ alkyl-;

R$^2$ is independently selected at each occurrence from —H, halogen, —C$_{1-10}$ alkyl, C$_{3-8}$ cycloalkyl-, aryl-C$_{0-8}$ alkyl- and C$_{1-4}$ alkoxy-C$_{0-8}$ alkyl-;

R$^3$ is independently selected at each occurrence from —H, —C$_{1-10}$ alkyl, C$_{3-8}$ cycloalkyl- and aryl-C$_{0-8}$ alkyl-;

R$^5$ is selected from:

(1) —OH,
(2) C$_{1-8}$ alkyloxy-,
(3) aryl-C$_{0-6}$ alkyloxy-,
(4) C$_{1-8}$ alkylcarbonyloxy-C$_{1-4}$ alkyloxy-, and
(5) aryl-C$_{1-8}$ alkylcarbonyloxy-C$_{1-4}$ alkyloxy-;

D is selected from —SO$_2$— and —C(O)—; and
R$^6$ is selected from:

(1) —C$_{1-6}$alkyl, unsusbstituted, mono- or di-substituted with R$^{1a}$,
(2) —(C$_{0-6}$alkyl)aryl, wherein the alkyl group is unsusbstituted, mono- or di-substituted with R$^{1a}$,
(3) —(C$_{0-6}$alkyl)heterocycle, wherein the alkyl group is unsusbstituted, mono- or di-substituted with R$^{1a}$,
(4) —NR$^1$(C$_{1-6}$alkyl), wherein the alkyl group is unsusbstituted, mono- or di-substituted with R$^{1a}$,
(5) —NR$^1$(C$_{0-6}$alkylaryl), wherein the alkyl group is unsusbstituted, mono- or di-substituted with R$^{1a}$,
(6) —NR$^1$(C$_{0-6}$alkylheterocycle), wherein the alkyl group is unsusbstituted, mono- or di-substituted with R$^{1a}$,
(7) —C$_{3-6}$ cycloalkyl,
(8) —CF$_3$,

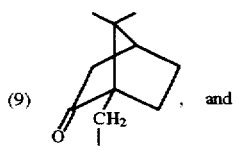

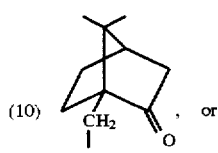

(11) when Z is unsubstituted or substituted phenyl, D-R$^6$ together with the nitrogen to which it is attached can form a bicyclic structure with Z (phenyl) as follows:

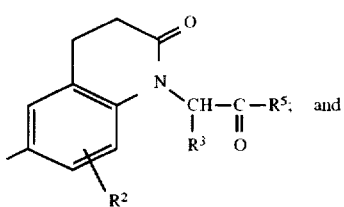

heterocycle is selected from a five or six membered saturated, partially unsaturated or aromatic ring which is unsubstituted, or monosubstituted or disubstituted with $R^{1a}$, and which consists of carbon atoms and one or two heteroatoms selected from the group —O—, —N—, —N($R^1$)— and —S—;

and wherein the remaining variables are as defined above in formula I.

In a second, further embodiment of this invention are compounds of formula II and the pharmaceutically acceptable salts, solvates and stereoisomers thereof wherein X-A- together represent a group selected from:

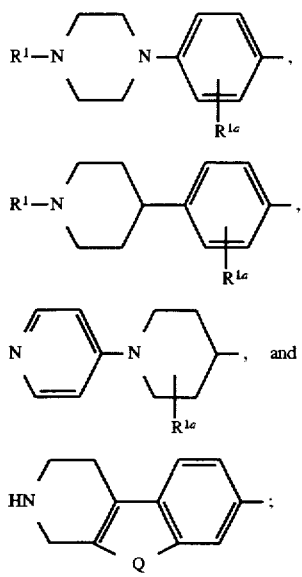

and the remaining variable are as defined above in formula II.

In a third, further embodiment of this invention are compounds of formula II and the pharmaceutically acceptable salts, solvates and stereoisomers thereof wherein X-A- together represent a group selected from:

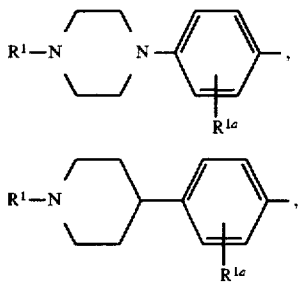

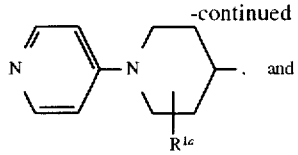

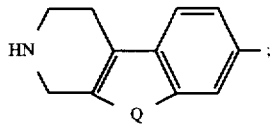

and the pharmaceutically acceptable salts, hydrates and stereoisomers thereof wherein:

Q is selected form —NH—, —O— and —S—;
Y is selected from:
(1) —$NR^1$—CO—,
(2) —$CONR^1$—,
(3) —O—,
(4) —$SO_p$—,
(5) —$NR^1$—,
(6) —$SO_p$—$NR^1$—,
(7) —CO—, and
(8) —CH(OH)—;
p is an integer selected from 0, 1 and 2;
Z is selected from:
(1) phenyl,
(2) phenyl which is mono-, di- or tri-substituted with $R^2$,
(3) thienyl,

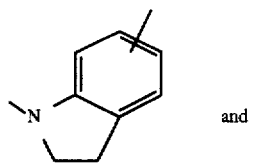

(4)

and

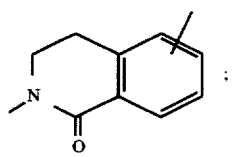

(5)

;

$R^1$ is independently selected at each occurrence from —H and —$C_{1-10}$ alkyl;
$R^{1a}$ is independently selected at each occurrence from —H, halogen and —$C_{1-10}$ alkyl;
$R^2$ is independently selected at each occurrence from —H, halogen and —$C_{1-10}$ alkyl;
$R^3$ is independently selected at each occurrence from —H and —$C_{1-10}$ alkyl;
$R^5$ is selected from:
(1) —OH,
(2) $C_{1-8}$ alkyloxy-,
(3) aryl-$C_{0-6}$ alkyloxy-,
(4) $C_{1-8}$ alkylcarbonyloxy-$C_{1-4}$ alkyloxy-, and
(5) aryl-$C_{1-8}$ alkylcarbonyloxy-$C_{1-4}$ alkyloxy-;
D is selected from —$SO_2$— and —C(O)—; and
$R^6$ is selected from:
(1) —$C_{1-6}$alkyl, unsusbstituted, mono- or di-substituted with $R^{1a}$,
(2) —($C_{0-6}$alkyl)aryl, wherein the alkyl group is unsusbstituted, mono- or di-substituted with $R^{1a}$, (3) —(C$_{0-6}$alkyl)heterocycle, wherein the alkyl group is unsusbstituted, mono- or di-substituted with R$^{1a}$, (4) —NR$^1$ (C$_{1-6}$alkyl), wherein the alkyl group is unsusbstituted, mono- or di-substituted with R$^{1a}$, (5) —NR$^1$(C$_{0-6}$alkylaryl), wherein the alkyl group is unsusbstituted, mono- or di-substituted with R$^{1a}$, (6) —NR$^1$(C$_{0-6}$alkylheterocycle), wherein the alkyl group is unsusbstituted, mono- or di-substituted with R$^{1a}$, (7) —C$_{3-6}$ cycloalkyl, (8) —CF$_3$,

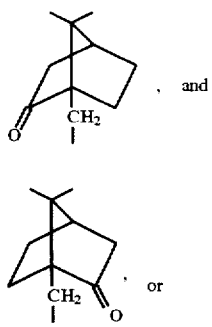
(9) and (10) or

(11) when Z is unsubstituted or substituted phenyl, D-R$^6$ together with the nitrogen to which it is attached can form a bicyclic structure with Z (phenyl) as follows:

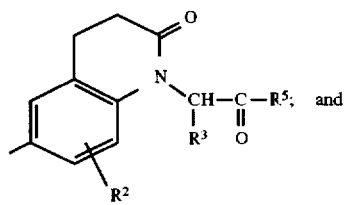

heterocycle is selected from a five or six membered saturated, partially unsaturated or aromatic ring which is unsubstituted, or monosubstituted or disubstituted with R$^{1a}$, and which consists of carbon atoms and one or two heteroatoms selected from the group —O—, —N—, —N(R$^1$)— and —S—;

and any remaining variables are as defined in formula II.

In a fourth, further embodiment of this invention are compounds of formula II having the particular formula III

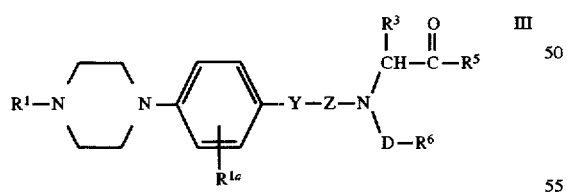

and the pharmaceutically acceptable salts, solvates and stereoisomers thereof wherein:

Y is selected from:

(1) —NR$^1$—CO—, (2) —CONR$^1$—, (3) —O—, (4) —SO$_p$—, (5) —NR$^1$—, (6) —SO$_p$—NR$^1$—, (7) —CO—, and (8) —CH(OH)—;

p is an integer selected from 0, 1 and 2;

Z is selected from:

(1) phenyl, (2) phenyl which is mono-, di- or tri-substituted with R$^2$, (3) thienyl,

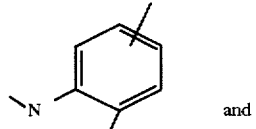
(4) and

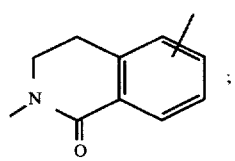
(5) ;

R$^1$ is independently selected at each occurrence from —H and —C$_{1-10}$ alkyl;

R$^{1a}$ is independently selected at each occurrence from —H, halogen and —C$_{1-10}$ alkyl;

R$^2$ is independently selected at each occurrence from —H, halogen and —C$_{1-10}$ alkyl;

R$^3$ is independently selected at each occurrence from —H and —C$_{1-10}$ alkyl;

R$^5$ is selected from:

(1) —OH, (2) C$_{1-8}$ alkyloxy-, (3) aryl-C$_{0-6}$ alkyloxy-, (4) C$_{1-8}$ alkylcarbonyloxy-C$_{1-4}$ alkyloxy-, and (5) aryl-C$_{1-8}$ alkylcarbonyloxy-C$_{1-4}$ alkyloxy-;

D is selected from —SO$_2$— and —C(O)—; and

R$^6$ is selected from:

(1) —C$_{1-6}$alkyl, unsusbstituted, mono- or di-substituted with R$^{1a}$, (2) —(C$_{0-6}$alkyl)aryl, wherein the alkyl group is unsusbstituted, mono- or di-substituted with R$^{1a}$, (3) —(C$_{0-6}$alkyl)heterocycle, wherein the alkyl group is unsusbstituted, mono- or di-substituted with R$^{1a}$, (4) —NR$^1$(C$_{1-6}$alkyl), wherein the alkyl group is unsusbstituted, mono- or di-substituted with R$^{1a}$, (5) —NR$^1$(C$_{0-6}$alkylaryl), wherein the alkyl group is unsusbstituted, mono- or di-substituted with R$^{1a}$, (6) —NR$^1$(C$_{0-6}$alkylheterocycle), wherein the alkyl group is unsusbstituted, mono- or di-substituted with R$^{1a}$, (7) —C$_{3-6}$ cycloalkyl, (8) —CF$_3$,

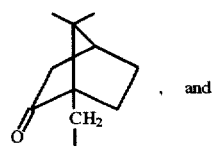
(9) and (10) or

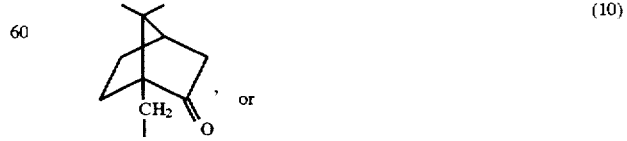

(11) when Z is unsubstituted or substituted phenyl, D-R$^6$ together with the nitrogen to which it is attached can form a bicyclic structure with Z (phenyl) as follows:

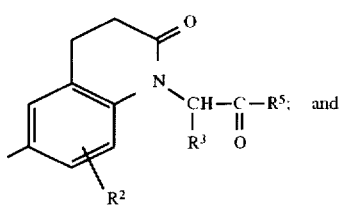

heterocycle is selected from a five or six membered saturated, partially unsaturated or aromatic ring which is unsubstituted, or monosubstituted or disubstituted with $R^{1a}$, and which consists of carbon atoms and one or two heteroatoms selected from the group —O—, —N—, —N($R^1$)— and —S—;

and the remaining variables are as defined in formula II.

In a fifth, further embodiment of this invention are compounds of formula III having the particular formula IV

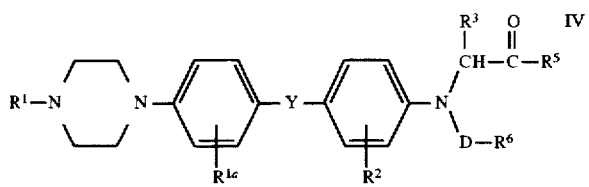

and the pharmaceutically acceptable salts, solvates and stereoisomers thereof wherein:

Y is selected from —C(O)—N($R^1$)— and —N($R^1$)—C(O)—;

$R^1$ is independently selected at each occurrence from —H and —$C_{1-10}$ alkyl;

$R^{1a}$ is independently selected at each occurrence from —H, halogen and —$C_{1-10}$ alkyl;

$R^2$ is independently selected at each occurrence from —H, halogen and —$C_{1-10}$ alkyl;

$R^3$ is independently selected at each occurrence from —H and —$C_{1-10}$ alkyl;

$R^5$ is selected from:
(1) —OH,
(2) $C_{1-8}$ alkyloxy-,
(3) aryl-$C_{0-6}$ alkyloxy-,
(4) $C_{1-8}$ alkylcarbonyloxy-$C_{1-4}$ alkyloxy-, and
(5) aryl-$C_{1-8}$ alkylcarbonyloxy-$C_{1-4}$ alkyloxy-;

D is selected from —$SO_2$— and —C(O)—; and $R^6$ is selected from:
(1) —$C_{1-6}$alkyl, unsusbstituted, mono- or di-substituted with $R^{1a}$,
(2) —($C_{0-6}$alkyl)aryl, wherein the alkyl group is unsusbstituted, mono- or di-substituted with $R^{1a}$,
(3) —($C_{0-6}$alkyl)heterocycle, wherein the alkyl group is unsusbstituted, mono- or di-substituted with $R^{1a}$,
(4) —$NR^1$($C_{1-6}$alkyl), wherein the alkyl group is unsusbstituted, mono- or di-substituted with $R^{1a}$,
(5) —$NR^1$($C_{0-6}$alkylaryl), wherein the alkyl group is unsusbstituted, mono- or di-substituted with $R^{1a}$,
(6) —$NR^1$($C_{0-6}$alkylheterocycle), wherein the alkyl group is unsusbstituted, mono- or di-substituted with $R^{1a}$, (7) —$C_{3-6}$ cycloalkyl,
(8) —$CF_3$,

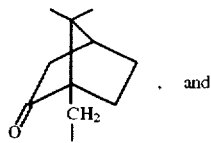

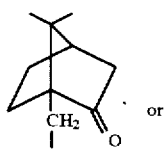

(11) when Z is unsubstituted or substituted phenyl, D-$R^6$ together with the nitrogen to which it is attached can form a bicyclic structure with Z (phenyl) as follows:

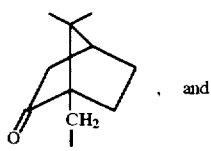

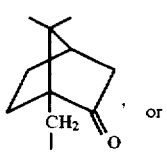

heterocycle is selected from a five or six membered saturated, partially unsaturated or aromatic ring which is unsubstituted, or monosubstituted or disubstituted with $R^{1a}$, and which consists of carbon atoms and one or two heteroatoms selected from the group —O—, —N—, —N($R^1$)— and —S—;

and any remaining variables are as defined in formula III.

In a sixth, further embodiment of this invention are compounds of formula IV wherein Y is selected from —C(O)—NH— and —NH—C(O)—; and $R^6$ is selected from (1) unsubstituted, mono and di-substituted phenyl, (2) methyl, (3) benzyl wherein the aryl portion may be unsubstituted, mono or di-substituted, and (4) thienyl; and any remaining variables are as defined in formula IV.

In one class of the instant six embodiments are compounds of formulas I, II, III, and IV as defined in the general definition wherein Y is —C(O)—NH—. Compounds in this class are exemplified, but not limited to, those of formula V as defined in Table I. The carbons around the phenyl rings in formula V have been arbitrarily numbered in order to clearly identify the substituent positions, where necessary.

TABLE I

[Structure V: piperazine-N-phenyl(R^1a)-C(O)-NH-phenyl(R^2)-N(CH2-C(O)-R^5)(D-R^6)]

V

| | $R^{1a}$ | $R^2$ | $R^5$ | D | $R^6$ |
|---|---|---|---|---|---|
| a) | H | H | $OCH_2CH_3$ | $-C(O)-$ | phenyl |
| b) | H | H | OH | $-C(O)-$ | $-CH_3$; |
| c) | H | H | OH | $-C(O)-$ | phenyl; |
| d) | H | H | $OCH_3$ | $-C(O)-$ | $-CH_3$; |
| e) | H | H | OH | $-C(O)-$ | 2-F-phenyl; |
| f) | H | H | OH | $-C(O)-$ | cyclopropyl; |
| g) | H | H | OH | $-C(O)-$ | 3-pyridinyl; |
| h) | H | H | OH | $-C(O)-$ | 4-pyridinyl; |
| i) | 6-$CH_3$ | H | OH | $-C(O)-$ | phenyl; |
| j) | H | 6-$CH_3$ | OH | $-C(O)-$ | phenyl; |
| k) | H | 5-$CH_3$ | OH | $-C(O)-$ | phenyl; |
| l) | H | H | OH | $-SO_2-$ | $-CF_3$; |
| m) | H | H | OH | $-SO_2-$ | 2-F-phenyl; |
| n) | H | H | $OC_2H_5$ | $-SO_2-$ | 2-thienyl; |
| o) | H | H | OH | $-SO_2-$ | 2-thienyl; |
| p) | H | H | OH | $-SO_2-$ | phenyl; |
| q) | H | 6-$CH_3$ | OH | $-SO_2-$ | phenyl; |
| r) | H | 2-Br | OH | $-SO_2-$ | 2-F-phenyl; |
| s) | H | H | OH | $-SO_2-$ | [camphor ketone structure]; |
| t) | H | H | OH | $-SO_2-$ | [camphor ketone structure]; and |
| u) | H | H | OH | $-C(O)-$ | $-CH_2-CH_2-$ bonded to D and the carbon denoted with * to form [dihydroquinolinone structure] |

In a second class of the instant embodiments are compounds of formulas I, II, III, and IV wherein Y is —NH—C(O)—. Compounds in this class are exemplified, but not limited to, those of formula VI as defined in Table II.

TABLE II

[Structure VI: piperazine-N-phenyl-NH-C(O)-Z-N(CH2-C(O)-R^5)(SO2-R^6)]

VI

| | Z | $R^5$ | $R^6$ |
|---|---|---|---|
| a) | 1,4-phenyl | OH | $CH_3$; |
| b) | 1,4-phenyl | $OCH_3$ | $CH_3$; |
| c) | 1,4-phenyl | $OCH(CH_3)_2$ | $CH_3$; |
| d) | 1,4-phenyl | OH | phenyl |

TABLE II-continued

[Structure VI]

VI

| | Z | $R^5$ | $R^6$ |
|---|---|---|---|
| e) | 1,4-phenyl | OH | 4-Br-phenyl; |
| f) | 1,4-phenyl | OH | benzyl; and |
| g) | 2,5-thienyl | OH | phenyl. |

Additional examples of compounds within the scope of this invention are shown below but are not limited to, those of formula VII as defined in Table III.

TABLE III

X—A—Y—Z—(CH₂)ₙ—N(CH₂—C(=O)—OH)(SO₂—Ph)

VII

| X-A | Y | Z | n |
|---|---|---|---|
| a) pyrazine-piperidine | —C(O)NH— | 1,4-phenyl | 0 |
| b) piperidine-phenyl (HN) | —C(O)NH— | 1,4-phenyl | 0 |
| c) piperidine-indole (HN) | —C(O)NH— | 1,4-phenyl | 0 |
| d) piperidine (HN) | —(CH₂)₂— | tetrahydroisoquinolinone | 1 |
| e) piperidine (HN) | —(CH₂)₃—O— | 1,4-phenyl | 1 |

When any substituent (e.g., $R^1$, $R^2$, etc.) occurs more than one time in any constituent, its definition on each occurrence is independent of its definition at any other occurrence. Also, combinations of substitutents and/or variables are permissible only if such combinations result in stable compounds.

As used herein "alkyl" is intended to include both branched- and straight-chain saturated aliphatic hydrocarbon groups having the specified number of carbon atoms, e.g., methyl (Me), ethyl (Et), propyl (Pr), butyl (Bu), pentyl, hexyl, heptyl, octyl, and the isomers thereof such as isopropyl (i-Pr), isobutyl (i-Bu), secbutyl (s-Bu), tertbutyl (t-Bu), isopentyl, isohexyl and the like. The term "cycloalkyl" is intended to include cyclized alkyl chains having the specified number of carbon atoms, e.g., cyclopropyl, cyclobutyl, cyclopentyl, cyclohexyl and cycloheptyl. "Alkoxy" or "alkyloxy" represents an alkyl group having the indicated number of carbon atoms attached through an oxygen bridge, e.g., methoxy, ethoxy, propyloxy, iso-propoxy, n-butoxy, iso-butoxy, sec-butoxy, t-butoxy and the like.

The specified number of carbon atoms in the appropriate groups described herein may include a zero in the range, e.g., $C_{0-6}$ or $C_{0-8}$. When a zero is in the specified range, it means that a bond is present in place of that carbon group.

The term halo or halogen is meant to include fluoro, chloro, bromo and iodo. The term "oxy" means an oxygen (O) atom.

The term "aryl" is defined above in the definition of Formula I; unsubstituted, mono-, di- and tri-substituted phenyl (Ph) is preferred.

The term heteroaryl is defined above in the definition of Formula I. The term heteroaryl encompasses a five or six-membered heteroaryl ring as defined in formula I fused to a benzene, pyridine or pyrimidine ring. Examples of heteroaryl groups include pyrrolyl, triazolyl, pyrazolyl, imidazolyl, pyridyl, pyrimidinyl, pyrazinyl, furanyl, pyranyl, thienyl, oxazolyl, isooxazolyl, thiazolyl, indolyl, benzimidazolyl, benzofuranyl, benzopyranyl, benzothienyl, quinolyl, isoquinolyl and the like. The heteroaryl ring may be attached within structural Formula I at any heteroatom or a carbon atom in the ring which results in the creation of a stable structure. Preferred heteroaryl groups include pyridyl, thiazolyl, oxazolyl, thienyl, indolyl, benzofuranyl, and benzothienyl.

The term "$C_{0-6}$ alkylaryl" as used herein includes an alkyl group as defined above bonded to an aryl group as defined above. The $C_{0-6}$ designation refers to the alkyl component of the alkylaryl unit. Examples of $C_{0-6}$ alkylaryl include phenyl-, benzyl-, fluorobenzyl-, chlorobenzyl-, phenylethyl-, phenylpropyl-, fluorophenylethyl-, and chlorophenylethyl-.

The term "$C_{0-6}$ alkylheterocycle" as used herein includes an alkyl group as defined above bonded to a heterocycle group as defined above. The $C_{0-6}$ designation refers to the alkyl component of the alkylheterocycle unit. Examples of $C_{0-6}$ alkylheterocycle include thienyl-, thienylmethyl-, thienylethyl-, and thienylpropyl-.

Amino acids suitable for compounds of the present invention include naturally occurring L- or D-amino acids, for example, those naturally occurring L-amino acids present in humans, e.g., protein amino acids, including L-alanine, L-arginine, L-asparagine, L-aspartic acid, L-cysteine, L-glutamine, L-glutamic acid, L-glycine, L-histidine, L-isoleucine, L-leucine, L-lysine, L-methionine, L-phenylalanine, L-proline, L-serine, L-threonine, L-tryptophan, L-tyrosine, and L-valine, and those naturally occurring D-amino acids which are non-protein amino acids, such as those found, for example, in antibiotic substances produced by bacteria and fungi, including D-valine, D-asparagine, D-glutamate, D-ornithine, D-phenylalanine, D-leucine, D-cysteine, and D-aspartate. (see Zubay "BIO-CHEMISTRY" Addison-Wesley Publishing Company, Inc. (Reading, Mass.) 1983 pp. 867–870 and Stryer "BIO-CHEMISTRY" W. H. Freeman and Company (New York, N.Y.) 3rd Edition 1988 pp. 16–21).

The term "pharmaceutically acceptable salts" shall mean non-toxic salts of the compounds of this invention which are generally prepared by reacting the free base with a suitable organic or inorganic acid. Representative salts include the following salts: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylbromide, methylnitrate, methylsulfate, mucate, napsylate, nitrate, oleate, oxalate, pamaote, palmitate, panthothenate, phosphate/diphosphate, polygalacturonate, salicylate, stearate, subacetate, succinate, tannate, tartrate, teoclate, tosylate, triethiodide, valerate.

Prodrugs, such as ester derivatives of described compounds, are compound derivatives which, when absorbed into the bloodstream of a warm-blooded animal, anabolize or cleave in such a manner as to release the drug form and permit the drug to afford improved therapeutic efficacy.

The compounds of the present invention are chiral and the present compounds may occur as racemates, racemic mixtures and as individual diasteriomers or enantiomers with all such isomeric forms being included within the scope of this invention. Furthermore, some of the crystalline forms for compounds of the present invention may exist as polymorphs and as such are intended to be included in the present invention. In addition, some of the compounds of the instant invention may form solvates with water or common organic solvents. Such solvates and hydrates, as well as anhydrous compositions, are encompassed within the scope of this invention.

The term "therapeutically effective amount" shall mean that amount of a drug or pharmaceutical agent that will elicit the biological or medical response of a tissue, system, animal or human that is being sought by a researcher, veterinarian, medical doctor or other clinician, which includes alleviation of the symptoms of the disease being treated. The term "mammal" includes humans.

The term "anti-coagulant" shall include heparin, and warfarin. The term "thrombolytic agent" shall include agents such as streptokinase and tissue plasminogen activator. The term "platelet anti-aggregation agent" shall include agents such as aspirin and dipyridamole.

The compounds of the present invention can be administered in such oral forms as tablets, capsules (each of which includes sustained release or timed release formulations), pills, powders, granules, elixirs, tinctures, suspensions, syrups, and emulsions. Likewise, they may be administered in intravenous (bolus or infusion), intraperitoneal, subcutaneous, or intramusculsar form, all using forms well known to those of ordinary skill in the pharmaceutical arts. An effective but non-toxic amount of the compound desired can be employed as an anti-aggregation agent.

Compounds of the invention may be administered to patients where prevention of thrombosis by inhibiting binding of fibrinogen to the platelet membrane glycoprotein complex IIb/IIIa receptor is desired. They are useful in surgery on peripheral arteries (arterial grafts, carotid endarterectomy) and in cardiovascular surgery where manipulation of arteries and organs, and/or the interaction of platelets with artificial surfaces, leads to platelet aggregation and consumption. The aggregated platelets may form thrombi and thromboemboli. Compounds of this invention may be administered to these surgical patients to prevent the formation of thrombi and thromboemboli.

Extracorporeal circulation is routinely used for cardiovascular surgery in order to oxygenate blood. Platelets adhere to surfaces of the extracorporeal circuit. Adhesion is dependent on the interaction between gp IIb/IIIa on the platelet membranes and fibrinogen adsorbed to the surface of the circuit. (Gluszko et al., Amer. J. Physiol., 252(H), 615–621 (1987)). Platelets released from artificial surfaces show impaired hemostatic function. Compounds of the invention may be administered to prevent adhesion.

Other applications of these compounds include prevention of platelet thrombosis, thromboembolism and reocclusion during and after thrombolytic therapy and prevention of platelet thrombosis, thromboembolism and reocclusion after angioplasty or coronary artery bypass procedures. They may also be used to prevent myocardial infarction.

The dosage regimen utilizing the compounds of the present invention is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of the present invention, when used for the indicated effects, will range between about 0.01 mg per kg of body weight per day (mg/kg/day) to about 100 mg/kg/day and preferably 0.01–100 mg/kg/day and most preferably 0.01–20 mg/kg/day. Typically, oral dosages for an adult patient are, for example, 1 mg, 10 mg or 100 mg. Intravenously, the most preferred doses will range from about 1 to about 10 mg/kg/minute during a constant rate infusion. Advantageously, compounds of the present invention may be administered in divided doses of two, three, or four times daily. Furthermore, preferred compounds for the present invention can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, or course, be continuous rather that intermittent throughout the dosage regime.

In the methods of the present invention, the compounds herein described in detail can form the active ingredient, and are typically administered in admixture with suitable pharmaceutical diluents, excipients or carriers (collectively referred to herein as "carrier" materials) suitably selected with respect to the intended form of administration, that is, oral tablets, capsules, elixirs, syrups and the like, and consistent with convention pharmaceutical practices. As such, a therapuetically effective amount of a compound of formula I can be used for the preparation of a medicament useful for inhibiting the binding of fibrinogen to blood platelets, inhibiting the aggregation of blood platelets, treating thrombus formation or embolus formation, or preventing thrombus or embolus formation in a mammal. For example, the medicament may be comprised of from 1 mg to 100 mgs of a compound of formula I, or more particularly, it may contain 1 mg, 10 mgs, 50 mgs, or 100 mgs of said compound.

Therapeutically effective amounts of a compound of formula I together with another active agent such as an anticoagulation agent or a thrombolytic agent can be used for the preparation of a medicament useful for inhibiting the binding of fibrinogen to blood platelets, inhibiting the aggregation of blood platelets, treating thrombus formation or embolus formation, or preventing thrombus or embolus formation in a mammal. Examples of other active agents which may be used include plasminogen activators or streptokinase, heparin, aspirin, warfarin, ticlopidine and/or clopidogrel.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water and the like. Moreover, when desired or necessary, suitable binders, lubricants, distintegrating agents and coloring agents can also be incorporated into the mixture. Suitable binders include starch, gelatin, natural sugars such as glucose or beta-lactose, corn-sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch methyl cellulose, agar, bentonite, xanthan gum and the like.

The compounds of the present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxy-propyl-methacrylamide-phenol, polyhydroxy-ethyl-aspartamide-phenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels.

The compounds of the present invention can also be co-administered with suitable anticoagulation agents or thrombolytic agents such as plasminogen activators or streptokinase in the treatment of various vascular pathologies. They may also be combined with heparin, aspirin, warfarin, ticlopidine and/or clopidogrel. Coadministration includes administration together at essentially the same time in a single dosage form or in separate dosage forms, or each agent administered at separately staggered times in order to achieve beneficial thrombosis prevention or thrombolysis.

The compounds of the present invention can be prepared readily according to the following Schemes and Examples or modifications thereof using readily available starting materials, reagents and conventional synthesis procedures. Those skilled in the art will readily understand that known variations of the conditions and processes of the following preparative procedures can be used to prepare these compounds. The examples are not intended to be limitations on the scope of the instant invention in any way, and they should not be so construed. Furthermore, the compounds described in the following examples are not to be construed as forming the only genus that is considered as the invention, and any combination of the compounds or their moieties may itself form a genus. Specific definitions of variables in the Schemes are illustrative only, and are not intended to limit the procedures described, unless otherwise noted. All temperatures are degrees Celsius unless otherwise noted.

Some abbreviations used herein are as follows: TBAF is tetrabutylammonium fluoride; DEAD is diethyl azodicarboxylate; $PPh_3$ is triphenyl phosphine. Many of the compounds described in the examples were analyzed by FAB mass spectroscopy (FABMS), and MS values are denoted.

In the schemes and examples below, various reagent symbols have the following meanings:

Ac: acyl ($CH_3$—C(O)—)
BOC (or Boc): t-butyloxycarbonyl
$BOC_2O$: di-t-butyl dicarbonate
BOP: Benzotriazol-1-yloxytris(dimethylamino) phosphonium, hexafluorophosphate
Bn: benzyl
n-BuLi: n-butyllithium
t-BuLi: tert-butyllithium
CBZ: Carbobenzyloxy
$CH_2Cl_2$: Methylene chloride
$CHCl_3$: chloroform
Pd-C: Palladium on activated carbon catalyst
DMF: Dimethylformamide
DMSO: Dimethylsulfoxide
EDC: 1-(3-Dimethylaminopropyl)-3-ethylcarbodiimide hydrochloride
EtOAc: ethyl acetate
EtOH: ethanol
HOAc: acetic acid
LDA: Lithium diisopropylamide
MeOH: methanol
NMM: N-methyl morpholine
NMP: N-methyl pyrrolidine
Oxone: potassium peroxymonosulfate
PYCLU: chloro N,N,N',N'-bis(pentamethylene) formamidinium hexafluorophosphate
RT: room temperature
TBDMS or TMS: t-butyldimethyl silyl
TFA: trifluoroacetic acid
THF: tetrahydrofuran;
TLC: thin layer chromatography

SCHEME 1

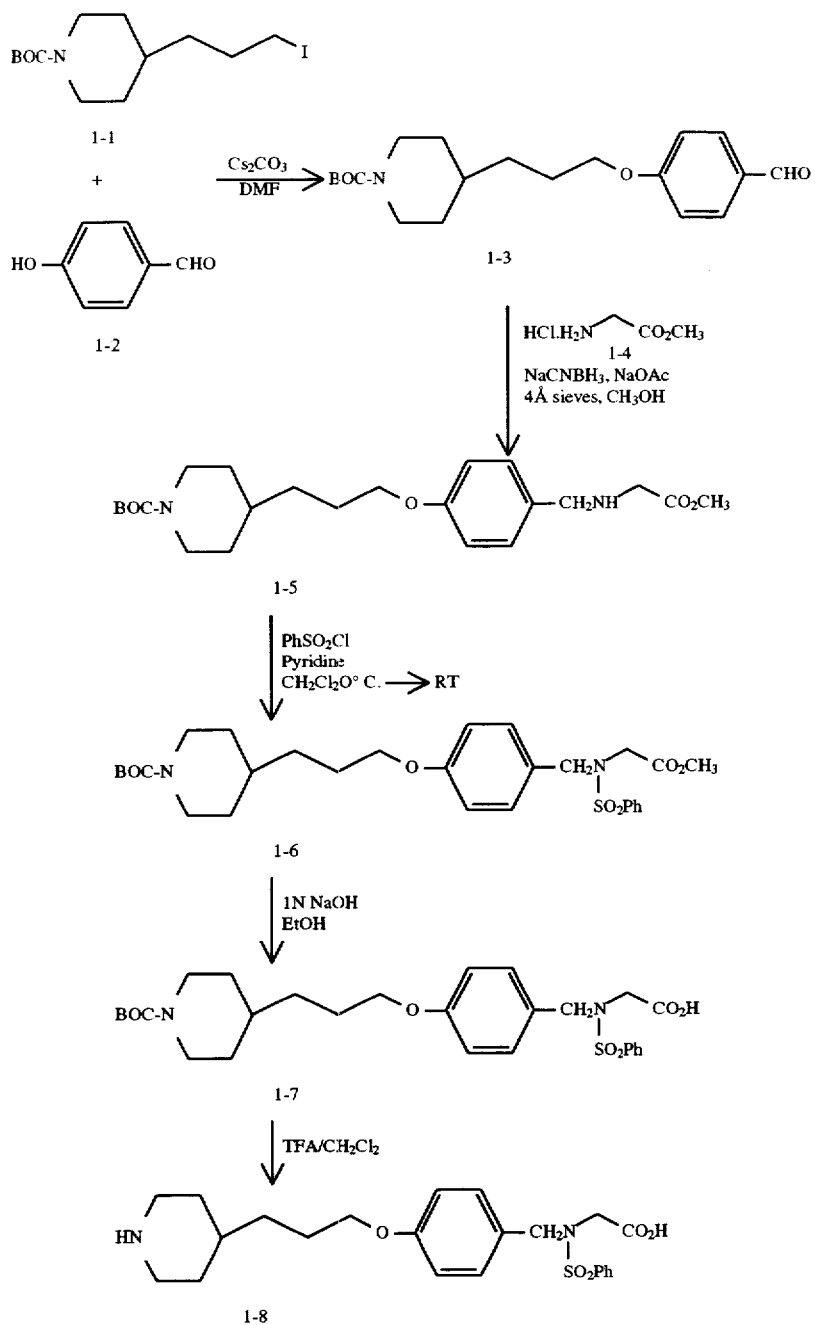

EXAMPLE 1

Step 1: 4-|3-(N-Boc-Piperidin-4-yl)propyloxy| benzaldehyde (1-3)

A solution of 3-(N-Boc-piperidin-4-yl)propyl iodide 1-1 (5.0 g, 14.2 mmol) (preparation described in EP 478,328), 4-hydroxybenzaldehyde 1-2 (1.73 g, 14.2 mmol), Cs2CO3 (9.2 g, 28.4 mmol) and DMF (50 ml) was stirred at ambient temperature for 2.0 hours. The reaction mixture was diluted with ethyl acetate and then washed with H$_2$O, sat. NaHCO$_3$, 10% KHSO$_4$, brine, dried (MgSO$_4$) and concentrated. Flash chromatography (silica, 10% EtOAc/hexane) provided 1-3 as a white solid.

TLC R$_f$ 0.80 (silica, 40% EtOAc/hexane)
$^1$H NMR (300 MHz, CDCl$_3$) δ 9.88 (s, 1H), 7.83 (d, J=9 Hz, 2H), 6.99 (d, J=9 Hz, 2H), 4.11 (m, 2H), 4.04 (t, J=6 Hz, 2H), 2.69 (bt, 2H), 1.84, (m, 2H), 1.69 (bd, 2H), 1.46 (m, 12H), 1.14 (m, 2H).

Step 2: N-|(3-(N-Boc-Piperidin-4-yl)propyloxy)phen-4-yl-methyl|glycine methyl ester (1-5)

To a stirred suspension of 4 Å molecular sieves (4 g) and CH$_3$OH (30 ml) was added NaOAc (1.18 g, 14.5 mmol), compound 1-3 (1.0 g, 2.89 mmol), amine 1-4 (363 mg, 2.89 mmol) and NaCNBH$_3$ (546 mg, 8.67 mmol). After 18 h, the reaction mixture was filtered through a celite pad. The pH of the resulting solution was adjusted to ~2 by the dropwise addition of conc. HCl to decompose excess hydride. The pH was adjusted to ~12 by the addition of $K_2CO_3$. The mixture was extracted with EtOAc. The organic portion was washed with brine, dried ($MgSO_4$) and concentrated. Flash chromatography (silica, 80% EtOAc/provided) amine 1-5 as a colorless oil.

TLC $R_f$ 0.32 (silica, EtOAc)

$^1$H NMR (300 MHz, $CD_3$)D) δ 7.22 (d, J=9 Hz, 2H), 6.85 (d, J=9 Hz, 2H), 4.10 (bd, 2H), 3.94 (t, J=6 Hz, 2H), 3.70 (m, 5H), 3.36 (s, 2H), 2.77 (m, 2H), 1.77 (m, 4H), 1.43 (m, 12H), 1.07 (m, 2H).

Step 3: N-[(3-(N-Boc-Piperidin-4-yl)propyloxy)phen-4-yl)-methyl]-N'-phenylsulfonyl glycine methyl ester (1-6)

To a stirred solution of amine 1-5 (900 mg, 2.15 mmol), pyridine (347 μL, 4.30 mmol) and $CH_2Cl_2$ (20 ml) at 0° C. was added phenylsulfonylchloride (300 μl, 2.37 mmol) followed by the removal of the cooling bath. After 18 h, the reaction was diluted with EtOAc and then washed with $H_2O$, 10% $KHSO_4$, brine, dried ($MgSO_4$) and concentrated. Flash chromatography (silica, 20% EtOAc/hexane) gave ester 1-6 as a colorless oil.

TLF $R_f$ 0.82 (silica, 50% EtOAc/hexane)

$^1$H NMR (300 MHz, $CDCl_3$) δ 7.88 (d, J=9H, 2H), 7.56 (m, 3H), 7.14 (d, J=9 Hz, 2H), 6.81 (d, J=9 Hz, 2H), 4.43 (s, 2H), 4.12 (m, 2H), 3.91 (m, 4H), 3.53 (s, 3H), 2.68 (bt, 2H), 1.79 (m, 2H), 1.68 (bd, 2H), 1.46 (m, 12H), 1.10 (m, 2H).

Step 4: N-[(3-(N-Boc-Piperidin-4-yl)propyloxy)phen4-yl-methyl]-N'-phenylsulfonyl glycine (1-7)

A solution of ester 1-6 (900 mg, 1.61 mmol), 1N NaOH (2 ml) and EtOH (5 ml) was stirred at ambient temperature for 30 minutes. The reaction mixture was then acidified with 10% $KHSO_4$, followed by extraction with EtOAc. The organic portion was washed with brine, dried ($MgSO_4$) and concentrated to give the carboxylic acid 1-7 as a white solid.

TLC $R_f$ 0.48 (silica, 9:0.5:0.5 $CH_2Cl_2$/MeOH/AcOH)

$^1$H NMR (300 MHz, $CD_3OD$) δ 7.87 (d, J=8 Hz, 2H), 7.59 (m, 3H), 7.09 (d, J=8 Hz, 2H), 6.82 (d, J=9H, 2H), 4.41 (s, 2H), 4.04 (bd, 2H), 3.93 (t, J=6 Hz, 2H), 3.84 (s, 2H), 2.76 (m, 2H), 1.79 (m, 4H), 1.44 (m, 12H), 1.04 (m, 2H).

Step 5: N-[(3-(Piperidin-4-yl)propyloxy)phen-4-yl-methyl]-N'-phenylsulfonyl glycine (1-8)

A solution of acid 1-7 (400 mg, 0.7334 mmol), TFA (3 ml) and $CH_2Cl_2$ (3 ml) was stirred at ambient temperature for 1.0 hour. The solution was concentrated and then azeotroped with toluene. Flash chromatography (silica, 20:1:1 EtOH/$NH_4OH$/$H_2O$) furnished amine 1-8 as a white solid.

TLC $R_f$ 0.41 (silica, 20:1:1 EtOH/$NH_4OH$/$H_2O$)

$^1$H NMR (300 MHz, NaOD/$D_2O$) δ 7.79 (d, J=8 Hz, 2H), 7.66 (d, J=7 Hz, 1H), 7.56 (t, J=8 Hz, 2H), 7.06 (d, J=8 Hz, 2H), 8.45 (d, J=9 Hz, 2H), 4.42 (s, 2H), 4.01 (t, J=8 Hz, 2H), 3.76 (s, 2H), 2.91 (m, 2H), 2.47 (t, J=12 Hz, 2H), 1.74 (m, 4H), 1.32 (m, 3H), 1.06 (m, 2H).

SCHEME 2

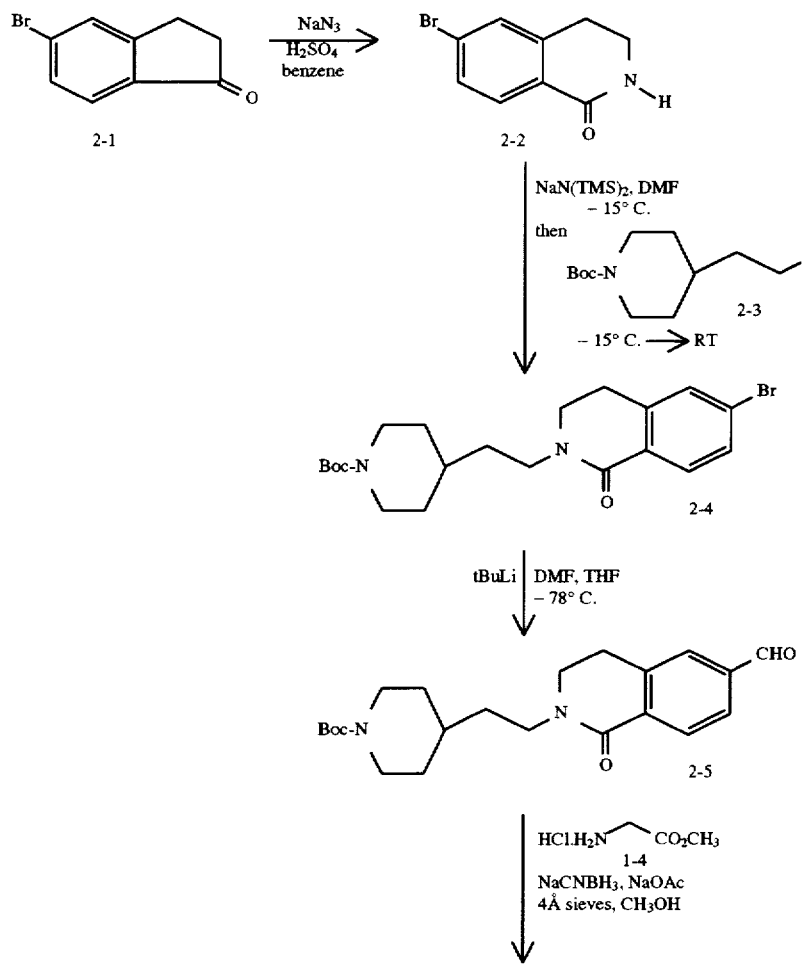

-continued
SCHEME 2

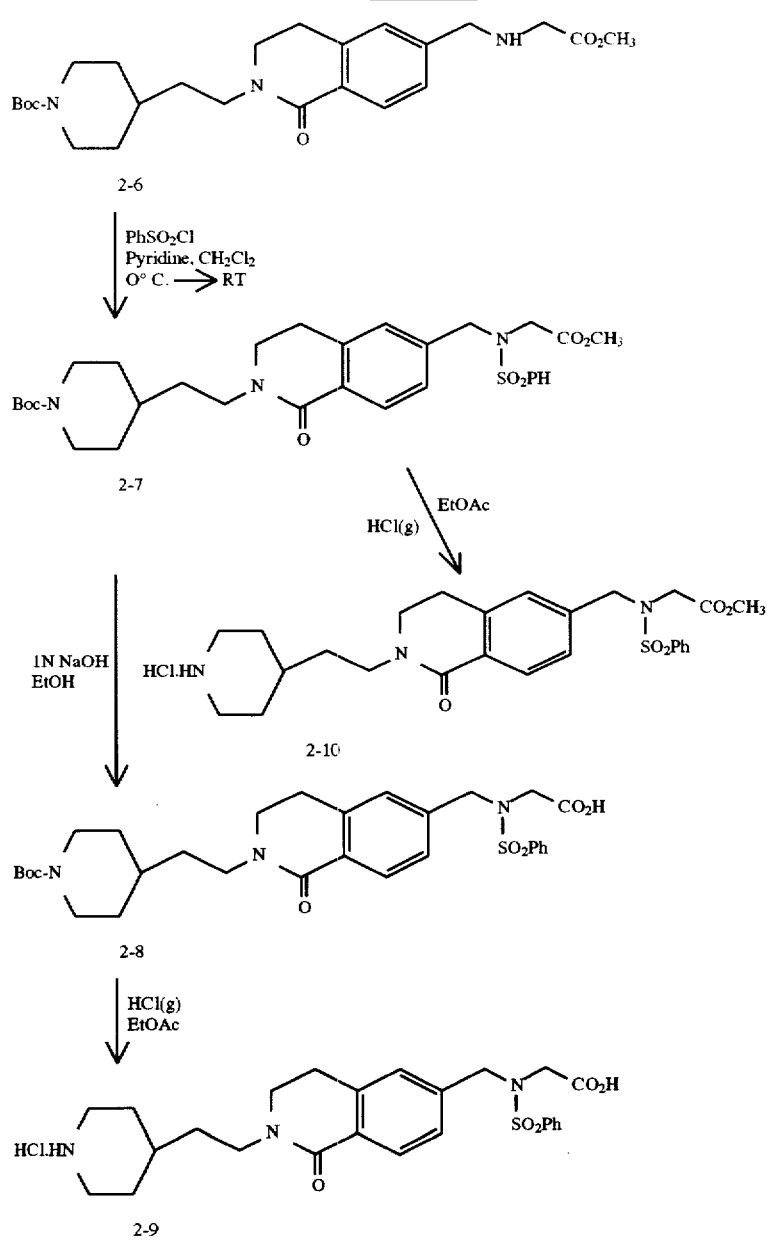

EXAMPLE 2

Step 1: 6-Bromo-3,4-dihydroisoquinolin-1-one (2-2)

To a stirred solution of bromide 2-1 (20.0 g, 94.8 mmol), $H_2SO_4$ (25.4 ml) and benzene (130 ml) at ambient temperature was added $NaN_3$ (8.88 g, 136.6 mmol) portionwise over a 30 minute period. After 1.0 hour, the reaction was diluted with EtOAc and then washed with $H_2O$, brine, dried ($MgSO_4$) and concentrated. Flash chromatography (silica, 40% EtOAc/hexanes→EtOAc) furnished bromide 2-2 as an orange solid.

TLC $R_f$ 0.31

$^1$H NMR (300 MHz, $CDCl_3$) δ 7.93 (d, J=8 Hz, 1H), 7.49 (d, J=8 Hz, 1H), 7.40 (s, 1H), 6.32 (bs, 1H), 3.57 (m, 2H), 2.99 (t, J=7 Hz, 2H).

Step 2: 6-Bromo-N-[(N-Boc-piperidin-4-yl)ethyl]-3,4,-dihydroisoquinolin-1-one (2-4)

To a stirred solution of bromide 2-2 (1.33 g, 5.88 mmol) and DMF (30 ml) at −15° C. was added NaN $(TMS)_2$ (1.0M/THF; 6.4 ml) dropwise over a 10 minute period. After 10 minutes, a solution of iodide 2-3 (2.0 g, 5.88 mmol) and DMF (4 ml) was added to the reaction mixture followed by the removal of the cooling bath. After 1.0 hour, the solution was diluted with EtOAc and then washed with 10% $KHSO_4$, brine, dried ($MgSO_4$) and concentrated. Flash chromatography (silica, 50% EtOAc/hexanes) afforded bromide 2-4 as a colorless oil.

TLC $R_f$ 0.23 (silica, 50% EtOAc/hexanes)

$^1$H NMR (300 MHz, $CDCl_3$) δ 7.93 (d, J=8 Hz, 1H), 7.46 (d, J=8 Hz, 1H), 7.35 (s, 1H), 4.12 (m, 2H), 3.56 (m, 4H), 2.97 (t, J=7 Hz, 2H), 1.69 (m, 3H), 1.54 (m, 2H), 1.45 (s, 9H), 1.13 (m, 2H).

Step 3: 6-Formyl-N-[(N-Boc-piperidin-4-yl)ethyl]-3,4-dihydroisoquinolin-1-one (2-5)

To a stirred solution of bromide 2-4 (1.90 g, 4.34 mmol), DMF (342 μl, 4.34 mmol) and THF (15 ml) at −78° C. was added t-BuLi (1.7M/pentane; 7.66 ml, 13.02 mmol) dropwise over a 5 minute period. After 1.0 hour, the reaction was quenched with AcOH. The solution was diluted with EtOAc and then washed with 10% KHSO$_4$, sat. NaHCO$_3$, brine, dried (MgSO$_4$) and concentrated. Flash chromatography (silica, 30%→50% EtOAc/hexanes) gave aldehyde 2-5 as a colorless oil.

TLC R$_f$ 0.13 (silica, 50% EtOAc/hexanes)

$^1$H NMR (300 MHz, CDCl$_3$) δ 10.06 (s, 1H), 8.24 (d, 8 Hz, 1H), 7.84 (d, J=8 Hz, 1H), 7.72 (s, 1H), 4.12 (m, 2H), 3.61 (m, 4H), 3.08 (t, J=7 Hz, 2H), 2.69 (t, 13 Hz, 2H), 1.75 (d, J=13 Hz, 2H), 1.59 (m, 2H), 1.45 (s, 10H), 1.19 (m, 2H).

Step 4: N-(N-[(N-Boc-Piperidin-4-yl)ethyl]-3,4-dihydroisoquinolin-1-one-6-yl-methyl)glycine methyl ester (2-6)

To a stirred suspension of 4 Å molecular sieves (3.60 g) and CH$_3$OH (30 ml) was added NaOAc (1.06 g, 12.95 mmol), benzaldehyde 2-5 (1.0 g, 2.59 mmol), amine 1-4 (326 mg, 2.59 mmol) and NaCNBH$_3$ (490 mg, 7.77 mmol). After 1.0 h, the reaction mixture was filtered through a celite pad. The pH of the resulting solution was adjusted to ~2 by the dropwise addition of 1N HCl. After 10 minutes, the pH was adjusted to ~12 by the addition of K$_2$CO$_3$. The mixture was extracted with EtOAc. The organic portion was washed with brine, dried (MgSO$_4$) and concentrated. Flash chromatography (silica, EtOAc) afforded amine 2-6 as a white solid.

TLC R$_f$ 0.09 (silica, EtOAc)

$^1$H NMR (300 MHz, CD$_3$OD) 7.89 (d, J=8 Hz, 1H), 7.33 (d, J=8 Hz, 1H), 7.26 (s, 1H), 4.07 (m, 2H), 3.81 (s, 2H), 3.72 (s, 3H), 3.60 (m, 4H), 3.40 (s, 2H), 3.00 (t, J=7 Hz, 2H), 2.73 (bt, 2H), 1.78 (bd, J=12 Hz, 2H), 1.61 (m, 2H), 1.44 (s, 10H), 1.10 (m, 2H).

Step 5: N-(N-[(N-Boc-Piperidin-4-yl)ethyl]3,4-dihydroisoquinolin-1-one-6-yl-methyl)-N'-phenylsulfonyl glycine methyl ester (2-7)

To a stirred solution of amine 2-6 (800 mg, 1.75 mmol), NMM (488 μl, 3.50 mmol) and CH$_2$Cl$_2$ (10 ml) at 0° C. was added benzenesulfonyl chloride (243 μl, 1.93 mmol) in a single portion followed by the removal of the cooling bath. After 48 h, the heterogeneous mixture was diluted with EtOAc and then washed with H$_2$O, sat. NaHCO$_3$, 10% KHSO$_4$, brine, dried (MgSO$_4$) and concentrated. Flash chromatography (silica, 50%→60% EtOAc/hexanes) furnished ester 2-7 as a white solid.

TLC R$_f$ 0.16 (silica, 50% EtOAc/hexanes)

$^1$H NMR (300 MHz, CD$_3$OD) δ 7.86 (m, 3H), 7.65 (d, J=7 Hz, 1H), 7.59 (d, J=9 Hz, 2H), 7.20 (d, J=8 Hz, 1H), 7.14 (s, 1H), 4.52 (s, 2H), 4.07 (m, 2H), 3.98 (s, 2H), 3.59 (m, 4H), 3.52 (s, 3H), 2.94 (t, J=8 Hz, 2H), 2.76 (m, 2H), 1.78 (bd, J=13 Hz, 2H), 1.57 (m, 2H), 1.44 (s, 10H), 1.15 (m, 2H).

Step 6: N-(N-[(N-Boc-Piperidin-4-yl)ethyl]-3,4-dihydroisoquinolin-1-one-6-yl-methyl)-N'-phenylsulfonyl glycine (2-8)

A solution of ester 2-7 (600 mg, 1.00 mmol), 1N NaOH (2.0 ml) and EtOH (5 ml) was stirred at ambient temperature for 1.5 hours. The reaction mixture was then acidified with 10% KHSO$_4$ followed by extraction with EtOAc. The organic portion was washed with brine, dried (MgSO$_4$) and concentrated to give acid 2-8 as a white solid.

$^1$H NMR (300 MHz, CD$_3$OD) δ 7.86 (m, 3H), 7.64 (d, J=7 Hz, 1H), 7.57 (d, J=9 Hz, 2H), 7.21 (d, J=8 Hz, 1H), 7.13 (s, 1H), 4.54 (s, 2H), 4.04 (bd, J=11 Hz, 2H), 3.93 (s, 2H), 3.59 (m, 4H), 2.94 (t, J=6 Hz, 2H), 2.73 (m, 2H), 1.76 (bd, J=13 Hz, 2H), 1.57 (m, 2H), 1.44 (s, 10H), 1.13 (m, 2H).

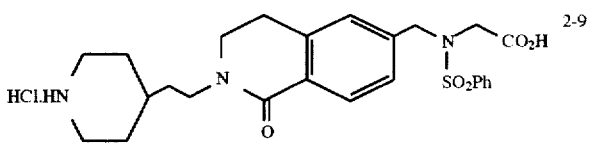

Step 7: N-(N-[(Piperidin-4-yl)ethyl]-3,4-dihydroisoquinolin-1-one-6-yl-methyl)-N'-phenylsulfonyl glycine (2-9)

EtOAc (8 ml) at 0° C. was treated with HCl (g) until saturated. A suspension of acid 2-8 (300 mg, 0.5124 mmol) and EtOAc (2 ml) was added in a single portion. After 30 minutes, argon was bubbled through the solution. The solvent was removed in vacuo to give amine 2-9 as a white solid.

$^1$H NMR (300 MHz, D$_2$O) δ 7.79 (d, J=8 Hz, 2H), 7.74 (m, 2H), 7.57 (m, 2H), 7.18 (d, J=8 Hz, 1H), 7.01 (s, 1H), 4.46 (s, 2H), 4.08 (s, 2H), 3.56 (m, 4H), 3.42 (bd, J=14 Hz, 2H), 2.96 (t, J=13 Hz, 2H), 2.86 (t, J=7 Hz, 2H), 2.03 (d, J=14 Hz, 2H), 1.64 (m, 3H), 1.45 (m, 2H).

EXAMPLE 2A

N-(N-[(Piperidin-4-yl)ethyl]-3,4-dihydroisoquinolin-1-one-6-yl-methyl)-N'-phenylsulfonyl glycine methyl ester hydrochloride (2-10)

EtOAc (8 ml) at 0° C. was treated with HCl (g) until saturated. A suspension of ester 2-7 (300 mg, 0.5004 mmol) and EtOAc (2 ml) was added in a single portion. After 30 minutes, argon was bubbled through the solution. The solvent was removed in vacuo to give amine 2-10 as a white solid.

$^1$H NMR (D$_2$O) δ 7.82 (d, J=8 Hz, 2H), 7.74 (m, 2H), 7.60 (t, J=8 Hz, 2H), 7.21 (d, J=8 Hz, 1H), 7.07 (s, 1H), 4.47 (s, 2H), 4.14 (s, 2H), 3.56 (m, 7H), 3.42 (d, J=13 Hz, 2H), 2.90 (m, 4H), 2.03 (d, J=14 Hz, 2H), 1.65 (m, 3H), 1.45 (m, 2H).

SCHEME 3

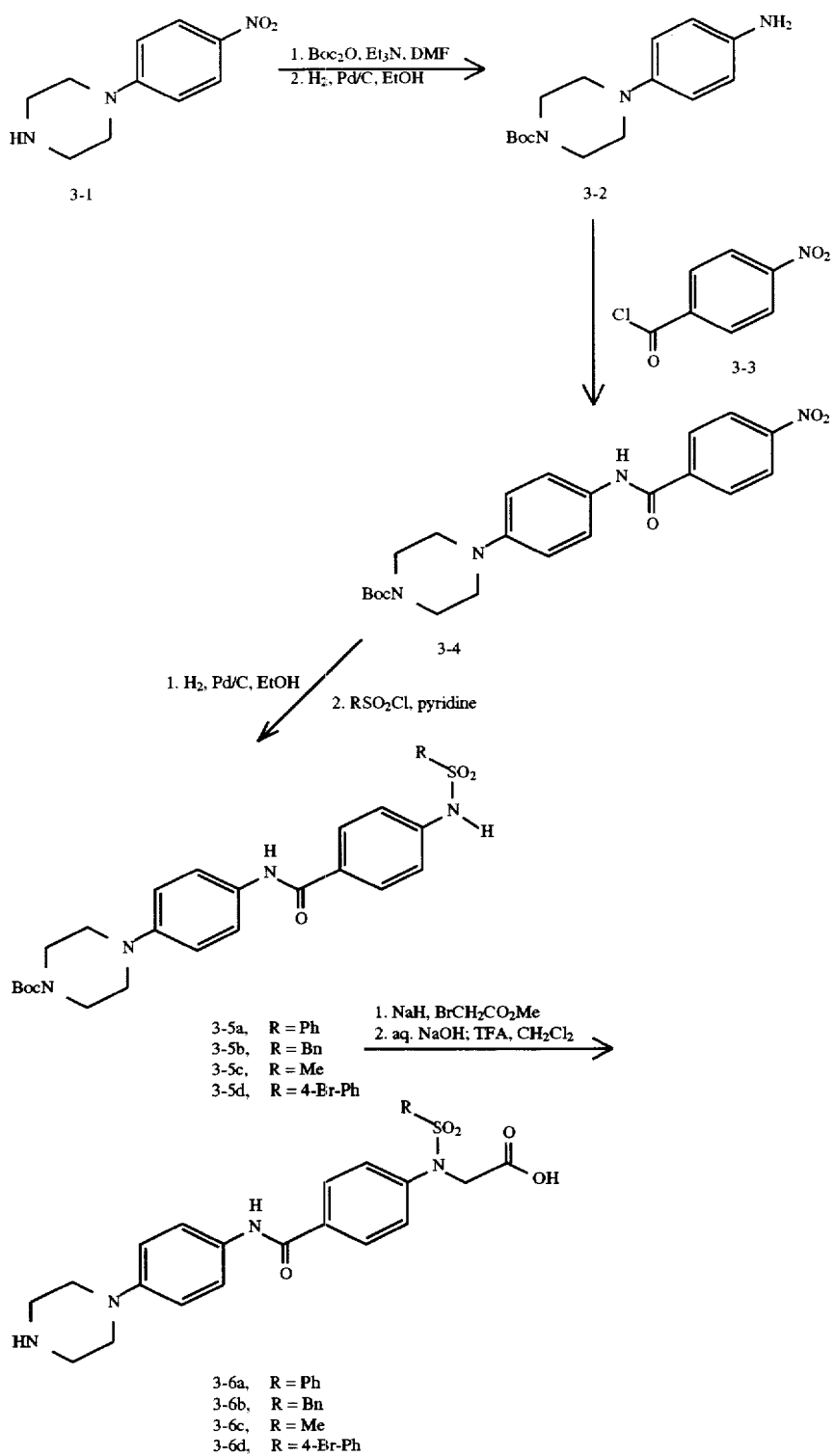

EXAMPLE 3A

Step 1: 4-(4-tert-Butyloxycarbonyl-piperazin-1-yl)aniline (3-2)

To a solution of 1-(4-nitrophenyl)piperazine (3-1) (9.8 g, 47.29 mmol) and triethylamine (7.3 mL, 52.37 mmol) in dichloromethane (175 mL) at RT, Boc$_2$O (11.38 g, 52.14 mmol) was added portionwise. The resultant mixture was stirred at RT for 2 h. The product mixture was concentrated under vacuum, and the residue triturated with hexane (150 mL). The resultant yellow powder was obtained by filtration.

Without further purification, the yellow solid was dissolved ethanol (200 mL) and shaken under an atmosphere of hydrogen gas at 50 psi in the presence of 0.8 g of 5% Pd/C for 18 h at RT. The product solution was filtered through a pad of Celite, and the filtrate was concentrated under vacuum to give 2 as pink solid.

Step 2: 4-[4-(4-tert-Butyloxycarbonyl-piperazin-1-yl) phenylaminocarbonyl]-nitrobenze (3-4)

To a suspension of 4-nitrobenzoic acid (4.06 g, 24.29 mmol) in dichloromethane (40 mL) and DMF (200 µL) at RT, oxalyl chloride (2.8 mL, 32 mmol) was added dropwise with a syringe pump over a period of 1 h. The resultant solution was stirred at RT for 0.5 h, and concentration under vacuum. The residue was dissolved in benzene and concentrated under vacuum to remove residual oxalyl chloride. The resultant 4-nitrobenzoyl chloride (3-3) was dissolved in dichloromethane (25 mL) and was added dropwisely to a cold (0° C.) solution of aniline 3-2 (6.12 g, 22.1 mmol) and DMAP (135 mg) in a mixture of dichloromethane (30 mL) and pyridine (4.5 mL) over a period of 30 min. The resultant slurry was diluted with dichloromethane (60 mL) and stirred at 0° C. for 1 h. The product mixture was further diluted with dichloromethane (600 mL), washed successively with sat. aq. sodium bicarbonate, sat aq. potassium hydrogen sulfate, water, and then brine until the aqueous extract was neutral. The dichloromethane solution was loaded directly onto a column of silica gel and the column eluted with ethyl acetate. Collection and concentration of appropriate fractions provided the amide 3-4.

Step 3: N-Phenylsulfonyl-4-[4-(4-tert-butyloxycarbonyl-piperazin-1-yl)-phenylaminocarbonyl]aniline (3-5a)

A suspension of the nitrobenzene 3-4 (6.9 g, 16.18 mmol) and 5% Pd/C.(0.93 g) in ethanol (110 mL) was shaken under an atmosphere of hydrogen gas at 50 psi overnight at RT. The resultant mixture was filtered through a plug of Celite, and washed repetitively with methanol (500 mL). The filtrate was concentrated under vacuum. The residue was treated with toluene and concentrated under vacuum to remove residual alcohols. The resultant aniline (4.49 g, 11.32 mmol) was treated with phenylsulfonyl chloride (1.75 mL, 13.7 mmol) in pyridine (15 mL) at 100° C. for 2 h. The resultant mixture was concentrated under vacuum. The residue was dissolved in methanol and concentrated onto silica gel. The resultant solid was loaded onto a column of silica gel and eluted with 80% ethyl acetate in hexane. Collection and concentration of appropriate fractions provided the sulfonamide 3-5a.

Step 4: N-{4-[4-(Piperazin-1-yl)phenylaminocarbonyl] phenyl}-N-phenyl-sulfonylglycine (3-6a)

To cold (0° C.) solution of the sulfonamide 3-5a (2.02 g, 3.76 mmol) in DMF (15 mL), sodium hydride (96 mg, 3.99 mmol) was added. The mixture was stirred at RT for 15 min. The resultant solution was cooled back to 0° C., and methyl bromoacetate (380 µL, 4.01 mmol) was added, and stirred at RT overnight. The product mixture was concentrated under vacuum, and the residue dissolved in ethyl acetate. The organic fraction was washed successively with aq. sodium bicarbonate and brine, dried over magnesium sulfate, filtered and concentrated under vacuum. The residue was subjected to column chromatography on silica gel eluting with 60% ethyl acetate in hexane. Collection and concentration of appropriate fractions provided N-4-[4(4-tert-butyloxycarbonyl-piperazin-1-yl)phenylaminocarbonyl] phenyl-N-phenylsulfonylglycine methyl ester.

To a solution of the glycine methyl ester (430 mg, 0.7 mmol) in a mixture of methanol (10 mL) and ethanol (3 mL) at RT, aq. sodium hydroxide (2.8 mL, 1M, 2.8 mmol) was added. The resultant mixture was stirred at RT for 5 h. The product mixture was concentrated, acidified with 1M hydrochloric acid, and extracted with ethyl acetate (3×70 mL). The organic extracts were combined, dried over sodium sulfate, filtered and concentrated under vacuum. The residue was dissolved in dichloromethane (7 mL) and treated with trifluoroacetic acid (3 mL) at RT for 2.5 h. The product solution was concentrated under vacuum. The residue was dissolved in water, frozen and lyophilized overnight to provide the sulfonylglycine 3-6a as a white fluffy solid.

$^1$H NMR (CD$_3$OD): δ 7.84 (2H, d, J=8.6 Hz), 7.71–7.49 (7H, m), 7.36 (2H, d, J=8.6 Hz), 7.03 (2H, J=9.0 Hz), 4.51 (2H, s), 3.38 (8H, br s).

Analysis calculated for C$_{25}$H$_{26}$N$_4$O$_5$S.1.30 TFA.0.20 H$_2$O C, 51.28; H, 4.32; N, 8.67 Found: C, 51.29; H, 4.31; N, 8.90

EXAMPLE 3B

Step 1: N-Benzylsulfonyl-4-[4-(4-tert-butyloxycarbonyl-piperazin-1-yl)-phenylaminocarbonyl]-aniline (3-5b)

Following the procedure described for 3-5a, but substituting benzylsulfonyl chloride for phenylsulfonyl chloride, 3-5b was prepared.

Step 2: N-{4-[4-(Piperazin-1-yl)phenylaminocarbonyl] phenyl}-N-benzyl-sulfonylglycine (3-6b)

Following the procedure described for 3-6a, but starting with N-benzylsulfonyl-4-[4-(4-tert-butyloxycarbonyl-piperazin-1-yl)-phenylaminocarbonyl]aniline (3-5b), 3-6b was prepared.

Analysis calculated for C$_{26}$H$_{28}$N$_4$O$_5$S.1.40 TFA.0.44 H$_2$O C, 51.16; H, 4.51; N, 8.29 Found: C, 51.16; H, 4.51; N, 8.55

EXAMPLE 3C

Step 1: N-Methylsulfonyl-4-[4-(4-tert-butyloxycarbonyl-piperazin-1-yl)-phenylaminocarbonyl]aniline (3-5c)

Following the procedure described for 3-5a, but substituting methanesulfonyl chloride for phenylsulfonyl chloride, 3-5c was prepared.

Step 2: N-{4-[4-(Piperazin-1-yl)phenylaminocarbonyl] phenyl}-N-methylsulfonylglycine (3-6c)

Following the procedure described for 3-6a, but starting with N-methylsulfonyl-4-[4-(t-tert-butyloxycarbonyl-piperazin-1-yl)phenylaminocarbonyl]aniline (3-5c), 3-6c was prepared.

Analysis calculated for C$_{20}$H$_{24}$N$_4$O$_5$S.1.48 TFA.0.14 H$_2$O C, 45.67; N, 4.30; N, 9.28 Found: C, 45.67; H, 4.30; N, 9.49

EXAMPLE 3D

Step 1: N4-bromo-phenylsulfonyl-4-[4-(4-tert-butyloxycarbonyl-piperazin-1-yl)-phenylaminocarbonyl] -aniline (3-5d)

Following the procedure described for 3-5a, but substituting 4-bromophenylsulfonyl chloride for phenylsulfonyl chloride, 3-5d was prepared.

Step 2: N-{4-[4-(piperazin-1-yl)phenylaminocarbonyl] phenyl}-N-4-bromo-phenyl-sulfonylglycine (3-6d)

Following the procedure described for 3-6a, but starting with N-4-bromo-phenylsulfonyl-4-[4-(4-tert-butyloxycarbonylpiperazin-1-yl)-phenylamino-carbonyl]-aniline (3-5d), 3-6d was prepared.

Analysis calculated for C$_{25}$H$_{25}$BrN$_4$O$_5$S.1.58 TFA.0.34 H$_2$O C, 44.52; H, 3.62; N, 7.37 Found: C, 44.51; H, 3.62; N, 7.50

SCHEME 4
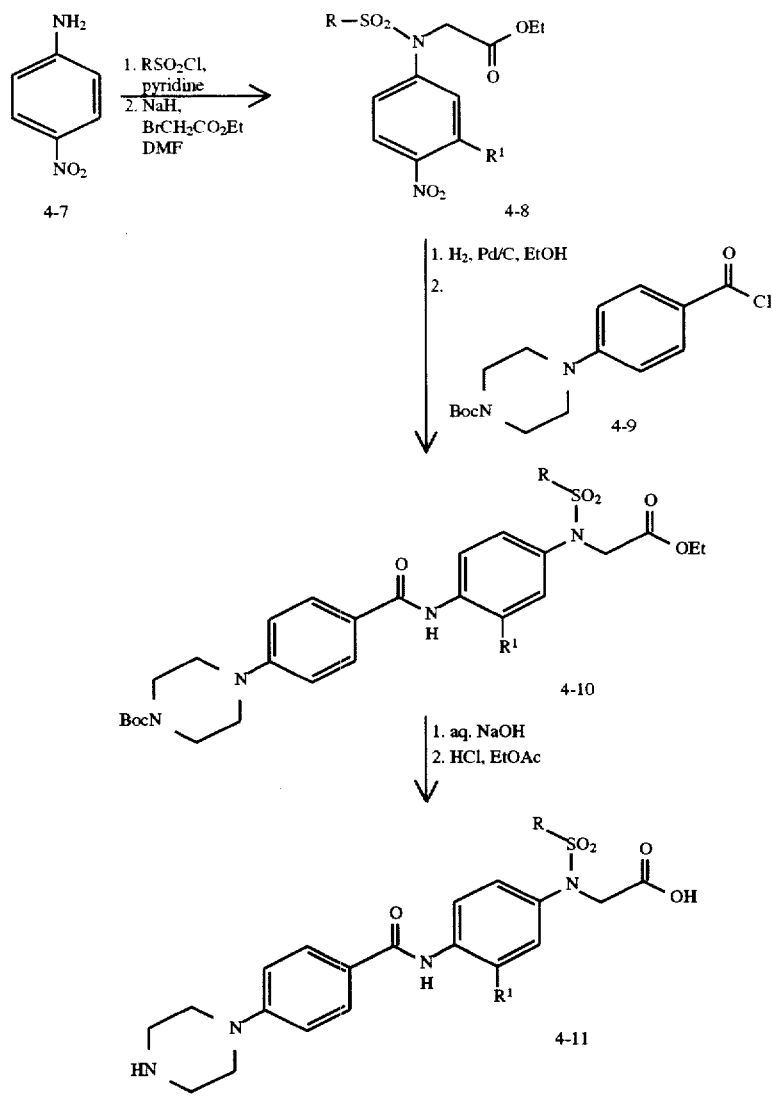
wherein the precursors (4-8, 4-10) and the corresponding final products (4-11) have R and $R^1$ defined as follows:
| Compound | R | $R^1$ |
|---|---|---|
| a) | Ph | H |
| b) | 2-thienyl | H |
| c) | 2-F—Ph | H |
| d) | 3-F—Ph | H |
| e) | 4-F—Ph | H |
| f) | Ph | $CH_3$ |
| g) | 2-F—Ph | Br |
| h) | $CF_3$ | H |
| i) | (R)-camphor | H |
| j) | (S)-camphor | H |

-continued
SCHEME 4

EXAMPLE 4A

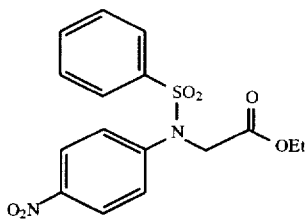

4-8a

Step 1: N-4-nitrophenyl-N-phenylsulfonylglycine ethyl ester (4-8a)

A solution of 4-nitroaniline (4-7) (13.8 g, 100 mmol) and phenylsulfonyl chloride (14 mL, 100 mmol) in pyridine (50 mL) was heated at 100° C. for 2 h. The resultant solution was concentrated, and the residue dissolved in ethyl acetate. The organic extract was washed successively with 2M hydrochloric acid, sat. aq. sodium bicarbonate brine, dried over magnesium sulfate, filtered and concentrated under vacuum. The residue was dissolved in a minimum amount of ethyl acetate with warning, and hexane added until the solution turned cloudy. The mixture was allowed to cool slowly to RT and then chilled at 0° C. The yellow solid precipitated was obtained by filtration. Further drying under vacuum overnight provide N-phenylsulfonyl-4-nitroaniline.

A cold (0° C.) solution of N-phenylsulphonyl-4-nitroaniline (7.39 g, 30 mmol) in DMF (65 mL) was treated with sodium hydride (0.76 g, 32 mmol) portionwise over a period of 1.5 h. A solution of ethyl bromoacetate (4 mL) in DMF (10 mL) was added, and the resultant mixture stirred at RT overnight. The product mixture was concentrated under vacuum, and the residue dissolved in ethyl acetate. The organic extract was washed with brine, dried over magnesium sulfate, filtered and concentrated under vacuum. The residue was subjected to column chromatography on silica gel eluting with 0.5% methanol in chloroform. Collection and concentration of appropriate fractions provided N-4-nitrophenyl-N-phenylsulfonylglycine ethyl ester (4-8a) as a clear gum.

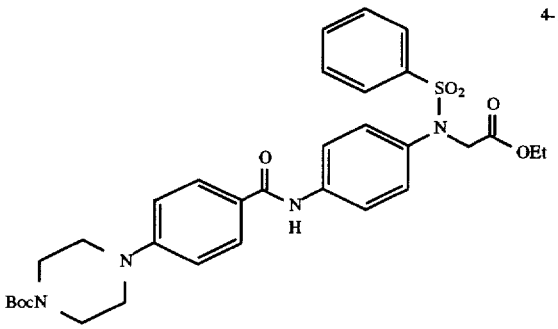

4-10a

Step 2: N-{4-|4-(4-tert-Butyloxycarbonylpiperazin-1-yl) phenylcarbonyl-amino|phenyl}-N-phenylsulfonylglycine ethyl ester (4-10a)

A solution of 4-8a (8.9 g, 24.4 mmol) in a mixture of ethanol (100 mL) and ethyl acetate (25 mL) was hydrogenated under an atmosphere of hydrogen gas at 45 psi in the presence of 5% Pd/C (0.89 g) at RT for 1.5 h. The resultant mixture was filtered through a plug of Celite, and the filtrate concentrated under vacuum. The residue was redissolved in toluene and concentrated under vacuum to provide the corresponding aniline.

A solution of 4-[4-(tert-butyloxycarbonyl)piperazin-1-yl] -benzoic acid (4-2 wherein $R^2$=H) (1.0 g, 3.3 mmol) in dichloromethane (25 mL) and DMF (3 drops) at RT was treated with oxalyl chloride (0.43 mL, 4.9 mmol) over a period of 10 min. The resultant solution was stirred at RT for 1 h, and concentrated under vacuum. The residue was dissolved in toluene and concentrated to remove residual oxalyl chloride. The resultant acid chloride 4-9 was redissolved in dichloromethane (5 mL), and added to a cold (0° C.) solution the above aniline (1.1 g, 3.3 mmol) and DMAP (0.48 g, 3.9 mmol) in dichloromethane (25 mL). The resultant mixture was stirred at RT overnight, diluted with dichloromethane and washed successively with 10% aq citric acid, sat. sodium bicarbonate, and brine. The organic extract was dried over magnesium sulfate, filtered and concentrated under vacuum. The residue was subjected to column chromatography on silica gel eluting with 50% ethyl acetate in hexane. Collection and concentration of appropriate fractions provided 4-10a as a gum.

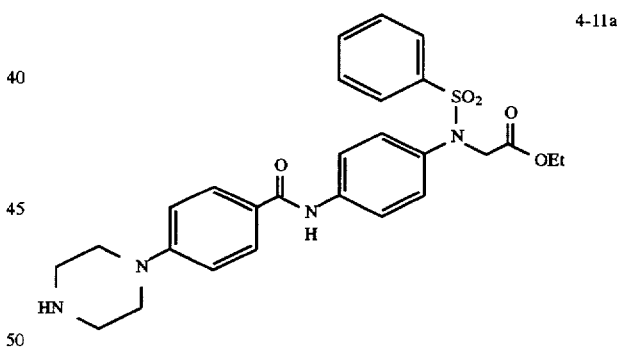

4-11a

Step 3: N-{4-|4-(Piperazin-1-yl)phenylcarbonylamino] phenyl}-N-phenyl-sulfonylglycine (4-11a)

To a solution of the glycine ethyl ester 4-10a (260 mg, 0.41 mmol) in methanol (2.5 mL), aq. sodium hydroxide (0.85 mL, 1M, 1.7 mmol) was added. The resultant mixture was stirred at RT for 2 h. The product mixture was concentrated, acidified, and extracted into dichloromethane. The combined organic extract were dried over sodium sulfate, filtered and concentrated under vacuum. The residue was dissolved in ethyl acetate (30 mL), cooled to 0° C., and treated with a steady stream of anhydrous hydrogen chloride gas for 10 min. The resultant solution was stirred at 0° C. for 1 h, and concentrated under vacuum. The residue was dissolved in water, frozen and lyophilized overnight to provide glycine 4-11a as a white fluffy solid.

$^1$H NMR (CD$_3$OD): δ 7.89 (2H, d, J=8.8 Hz), 7.69–7.50 (7H, m), 7.17 (2H, d, J=8.8 Hz), 7.11 (2H, d, J=9.0 Hz), 4.42 (2H, s), 3.6 (4H, m), 3.4 (4H, m).

39

Analysis calculated for $C_{25}H_{26}N_4O_5S.0.15$ EtOAc C. 51.34; H. 5.00; N. 9.35 Found: C. 51.34; H. 4.96; N. 9.30

EXAMPLE 4B

Following the procedures described in Example 4A. Steps 1-3, but substituting the appropriate reagents as described below, the following compounds were made:

(1) N-{4-[4-(Piperazin-1-yl)phenylcarbonylamino]phenyl}-N-thienylsulfonylglycine (4-11b)

This product was prepared using 2-thiophene sulfonyl chloride in place of phenylsulfonyl chloride in Step 1.

Analysis calculated for $C_{25}H_{26}N_4O_5S.1.40$ TFA.0.15 $H_2O$ C. 46.74; H. 3.91; N. 8.45 Found: C. 46.73; H. 3.92; N. 8.72

(2) N-{4-[4-(Piperazin-1-yl)phenylcarbonylamino]phenyl}-N-2-fluoro-phenyl-sulfonylglycine (4-11c)

This product was prepared using 2-fluorophenyl-sulfonyl chloride in place of phenylsulfonyl chloride in Step 1.

Analysis calculated for $C_{25}H_{25}FN_4O_5S.1.60$ TFA C. 48.74; H. 3.86; N. 8.06 Found: C. 48.37; H. 3.92; N. 8.46

(3) N-{4-[4-(Piperazin-1-yl)phenylcarbonylamino]phenyl}-N-3-fluoro-phenylsulfonylglycine (4-11d)

This product was prepared using 3-fluorophenylsulfonyl chloride in place of phenylsulfonyl chloride in Step 1.

Analysis calculate for $C_{25}H_{25}FN_4O_5S.1.30$ TFA.0.35 $H_2O$ C. 49.69; H. 4.08; N. 8.40 Found: C. 49.68; H. 4.04; N. 8.44

(4) N-{4-[4-(Piperazin-1-yl)phenylcarbonylamino]phenyl}-N-4-fluorophenyl-sulfonylglycine (4-11e)

This product was prepared using 4-fluorophenylsulfonyl chloride in place of phenylsulfonyl chloride in Step 1.

Analysis calculated for $C_{25}H_{25}FN_4O_5S.1.35$ TFA.0.35 $H_2O$ C. 49.45; H. 4.05; N. 8.33 Found: C. 49.45; H. 4.00; N. 8.40

(5) N-{4-[4-(Piperazin-1-yl)phenylcarbonylamino]-3-methylphenyl}-N-phenylsulfonyl glycine (4-11f)

This product was prepared using 3-methyl-4-nitroaniline in place of 4-nitroaniline in Step 1.

Analysis calculated for $C_{26}H_{28}N_4O_5S.1.40$ TFA.0.42 $H_2O$ C. 51.19; H. 4.51; N. 8.29 Found: C. 51.17; H. 4.51; N. 8.53

(6) N-{4-[4-(Piperazin-1-yl)phenylcarbonylamino]-3-bromophenyl}-N-2-fluoro-phenylsulfonylglycine (4-11g)

This product was made using 3-bromo-4-nitroaniline and 2-fluorophenylsulfonyl chloride in place of 4-nitroaniline and phenylsulfonyl chloride, respectively, in Step 1.

Analysis calculated for $C_{25}H_{24}BrFN_4O_5S.1.50$ TFA.0.35 $H_2O$ C. 43.75; H. 3.44; N. 7.29 Found: C. 43.76; H. 3.41; N. 7.53

(7) N-{4-[4-(Piperazin-1-yl)phenylcarbonylamino]phenyl}-N-trifluoro-methylsulfonylglycine (4-11h)

This product was prepared using trifluoromethanesulfonic anhydride and tert-butyl bromoacetate in place of phenylsulfonyl chloride and ethylbromo acetate, respectively, in Step 1.

40

Analysis calculated for $C_{20}H_{21}F_3N_4O_5S.1.25$ TFA.0.35 $H_2O$ C. 42.54; H. 3.64; N. 8.82 Found: C. 42.55; H. 3.60; N. 9.05

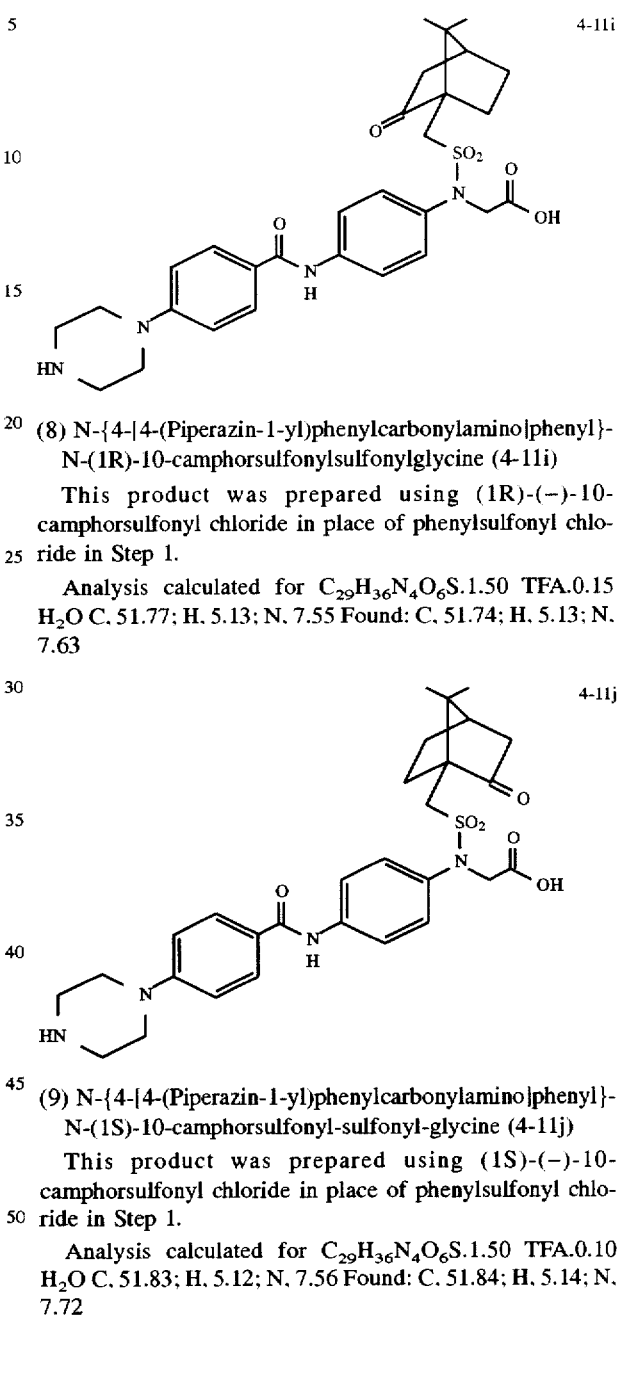

(8) N-{4-[4-(Piperazin-1-yl)phenylcarbonylamino]phenyl}-N-(1R)-10-camphorsulfonylsulfonylglycine (4-11i)

This product was prepared using (1R)-(−)-10-camphorsulfonyl chloride in place of phenylsulfonyl chloride in Step 1.

Analysis calculated for $C_{29}H_{36}N_4O_6S.1.50$ TFA.0.15 $H_2O$ C. 51.77; H. 5.13; N. 7.55 Found: C. 51.74; H. 5.13; N. 7.63

(9) N-{4-[4-(Piperazin-1-yl)phenylcarbonylamino]phenyl}-N-(1S)-10-camphorsulfonyl-sulfonyl-glycine (4-11j)

This product was prepared using (1S)-(−)-10-camphorsulfonyl chloride in place of phenylsulfonyl chloride in Step 1.

Analysis calculated for $C_{29}H_{36}N_4O_6S.1.50$ TFA.0.10 $H_2O$ C. 51.83; H. 5.12; N. 7.56 Found: C. 51.84; H. 5.14; N. 7.72

SCHEME 5
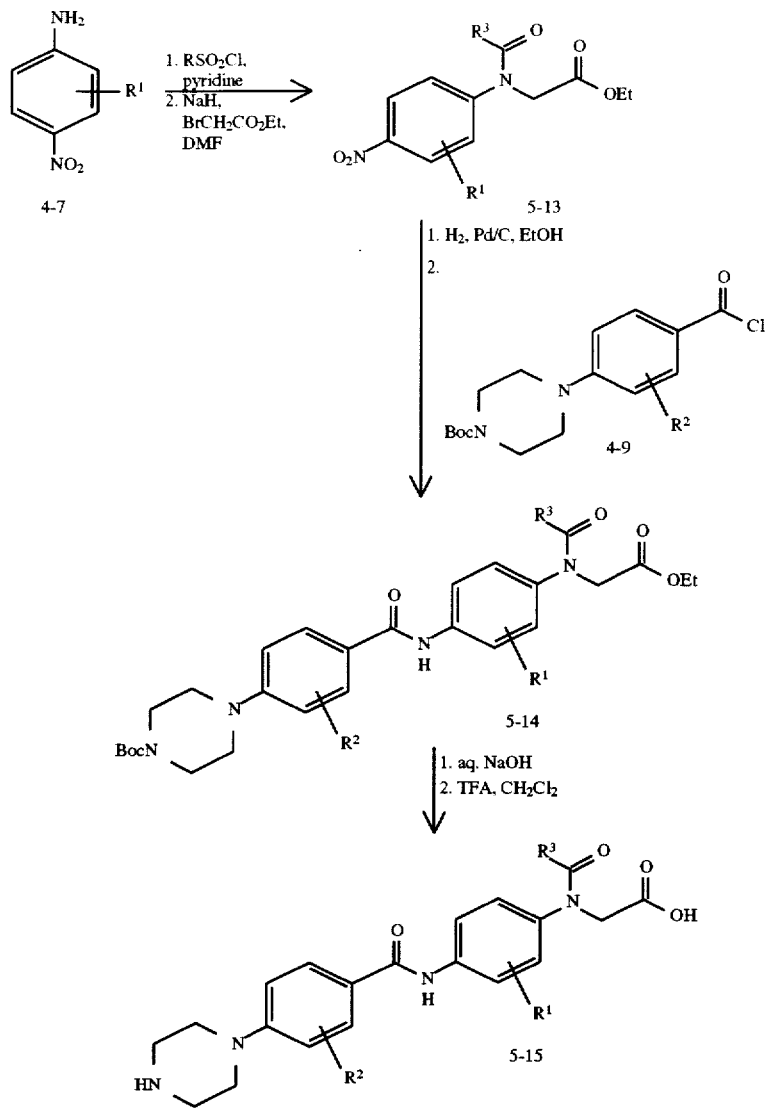
wherein the precursors (5-13, 5-14 and 4-9) and the corresponding final products (5-15) have $R^1$, $R^2$ and $R^3$ defined as follows:
| Cmpd | R | $R^1$ | $R^3$ |
|---|---|---|---|
| a) | H | H | Ph |
| b) | H | H | 2-F—Ph |
| c) | H | H | 3-F—Ph |
| d) | H | H | 4-F—Ph |
| e) | H | H | 2-pyridyl |
| f) | H | H | 3-pyridyl |
| g) | H | H | 4-pyridyl |
| h) | H | H | $CH_3$ |
| i) | H | H | ◁ |
| j) | H | H | $CH_2OCH_2Ph$ |
| k) | H | H | $CH_2OH$ |
| l) | 3-$CH_3$ | H | Ph |
| m) | 2-$CH_3$ | H | Ph |
| n) | H | 3-$CH_3$ | Ph |
| o) | H | 2-$CH_3$ | Ph |

-continued
SCHEME 5

EXAMPLE 5A

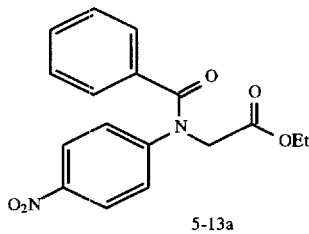

5-13a

Step 1: N-4-Nitrophenyl-N-benzoylglycine ethyl ester (5-13a)

A mixture of 4-nitroaniline (4-7) (10.0 g, 72 mmol) and anhydrous potassium carbonate (20 g, 1.44 mmol) in anhydrous THF (240 mL) and benzoyl chloride (9.1 mL, 78 mmol) was stirred at RT overnight. The resultant solution was poured into 10% aq. HCl (200 mL) and cooled to 0° C. The yellow solid precipitated was filtered, washed successively with water (200 mL) and hexane (200 mL). Further drying under vacuum overnight provided the required 4-nitro-N-benzoylaniline.

A cold (0° C.) solution of the above nitro aniline (4.8 g, 19.8 mmol) in DMF (40 mL) was treated portionwise with sodium hydride (0.48 g, 20 mmol). After the mixture was stirred at 0° C. for 0.5 h, a solution of ethyl bromoacetate (2.6 mL, 23.4 mmol) in DMF (20 mL) was added. The resultant mixture was stirred at 50° C. overnight and concentrated under vacuum. The residue was partitioned between ethyl acetate and water. The organic extract was washed with brine, dried over magnesium sulfate, filtered, and concentrated under vacuum to provide the nitrophenyl glycine ester 5-13a.

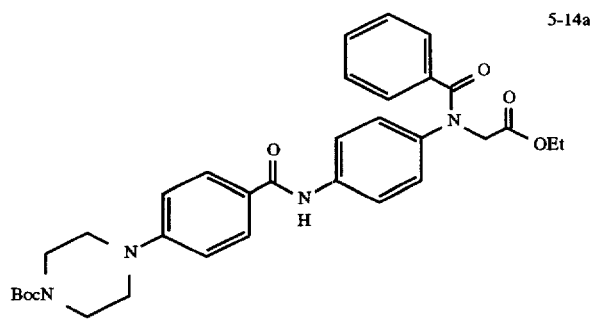

5-14a

Step 2: N-{4-|4-(4-tert-Butyloxycarbonyl-piperazin-1-yl)-phenylcarbonyl-amino|phenyl}-N-benzoylglycine ethyl ester (5-14a)

Following the procedure described for 4-10a, but substituting N-4-nitrophenyl-N-benzoyl-glycine ethyl ester (5-13a) for N-4-nitrophenyl-N-phenylsulfonyl-glycine ethyl ester (4-8a), 5-14a was prepared.

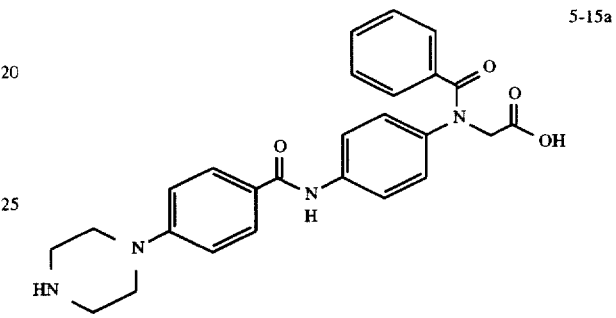

5-15a

Step 3: N-{4-|4-(Piperazin-1-yl)phenylcarbonylamino| phenyl}-N-benzoyl-glycine (5-15a)

Following the procedure described for 4-11a, but substituting N-{4-|4-(4-tert-butyloxycarbonylpiperazin-1-yl) phenyl-carbonylamino|phenyl}-N-benzoylglycine ethyl ester (5-14a) for N-{4-|4-(4-tert-butyloxycarbonylpiperazin-1-yl)phenylcarbonyl-amino| phenyl}-N-phenylsulfonylglycine ethyl ester (4-10a), 5-15a was prepared.

Analysis calculated for $C_{26}H_{26}N_4O_4 \cdot 1.35$ TFA$\cdot 0.30$ $H_2O$ C, 55.79; H, 4.56; N, 9.07 Found: C, 55.76; H, 4.57; N, 9.29

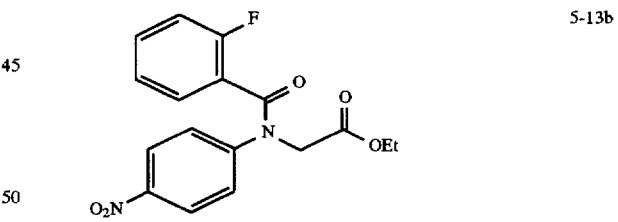

5-13b

Step 1: N-4-Nitrophenyl-N-2-fluorobenzoyl-glycine ethyl ester (5-13b)

Following the procedure described for 5-13a, but substituting 2-fluorobenzoyl chloride for benzoyl chloride, 5-13b was prepared.

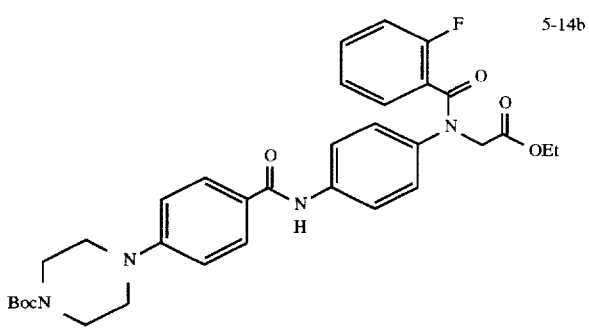

Step 2: N-{4-|4-(4-tert-Butyloxycarbonyl-piperazin-1-yl)-phenylcarbonyl-amino|phenyl}-N-2-fluorobenzoylglycine ethyl ester (5-14b)

Following the procedure described for 4-10a, but substituting N-4-nitrophenyl-N-2-fluorobenzoyl-glycine ethyl ester (5-13b) for N-4-nitrophenyl-N-phenylsulfonylglycine ethyl ester (4-8a), 5-14b was prepared.

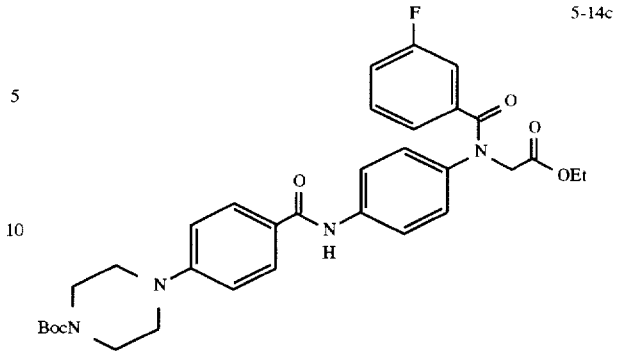

Step 2: N-{4-|4-(4-tert-Butyloxycarbonyl-piperazin-1-yl)-phenylcarbonyl-amino|phenyl}-N-3-fluorobenzoylglycine ethyl ester (5-14c)

Following the procedure described for 4-10a, but substituting N-4-nitrophenyl-N-3-fluorobenzoyl-glycine ethyl ester (5-13c) for N-4-nitrophenyl-N-phenylsulfonylglycine ethyl ester (4-8a), 5-14c was prepared.

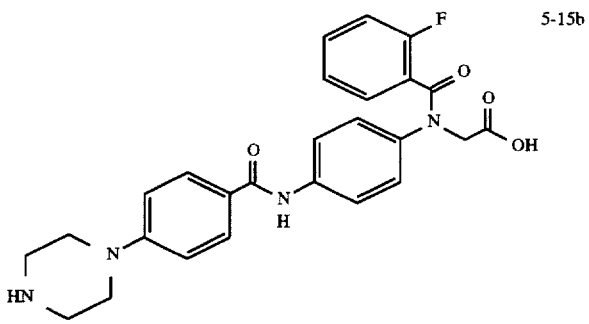

Step 3: N-{4-|4-(Piperazin-1-yl)phenylcarbonylamino|phenyl}-N-2-fluoro-benzoylglycine (5-15b)

Following the procedure described for 4-11a, but substituting N-{4-|4-(4-tert-butyloxycarbonyl-piperazin-1-yl)-phenylcarbonylamino|phenyl}-N-2-fluorobenzoyl-glycine ethyl ester (5-14b) for N-{4-|4-(4-tert-butyloxycarbonyl-piperazin-1-yl)-phenylcarbonylamino|phenyl}-N-phenylsulfonylglycine ethyl ester (4-10a), 5-15b was prepared.

Analysis calculated for $C_{26}H_{25}FN_4O_4 \cdot 1.35$ TFA $\cdot 0.15$ $H_2O$ C, 54.45; H, 4.24; N, 8.85 Found: C, 54.45; H, 4.26; N, 8.78

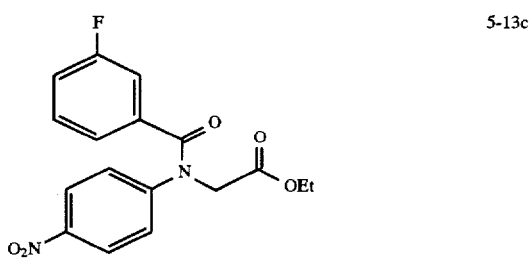

Step 1: N-4-Nitrophenyl-N-3-fluorobenzoylglycine ethyl ester (5-13c)

Following the procedure described for 5-13a, but substituting 3-fluorobenzoyl chloride for benzoyl chloride, 5-13c was prepared.

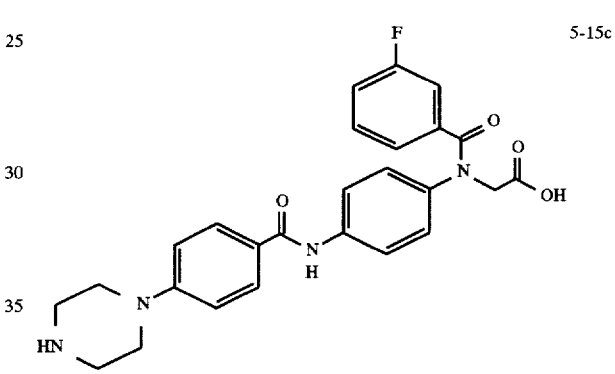

Step 3: N-{4-|4-(piperazin-1-yl)phenylcarbonylamino|phenyl}-N-3-fluoro-benzoylglycine (5-15c)

Following the procedure described for 4-11a, but substituting N-{4-|4-(4-tert-butyloxycarbonyl-piperazin-1-yl)-phenylcarbonylamino|phenyl}-N-3-fluorobenzoyl-glycine ethyl ester (5-14c) for N-{4-|4-(4-tert-butyloxycarbonyl-piperazin-1-yl)-phenylcarbonylamino|phenyl}-N-phenylsulfonylglycine ethyl ester (4-10a), 5-15c was prepared.

Analysis calculated for $C_{26}H_{25}FN_4O_4 \cdot 1.70$ TFA $\cdot 0.35$ $H_2O$ C, 52.19; H, 4.08; N, 8.28 Found: C, 52.19; H, 4.08; N, 8.42

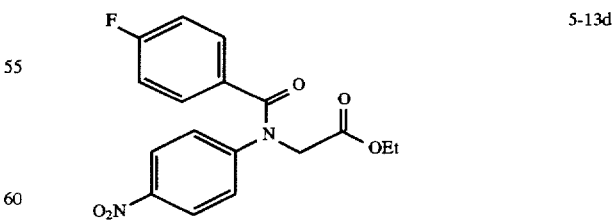

Step 1: N-4-Nitrophenyl-N-4-fluorobenzoylglycine ethyl ester (5-13d)

Following the procedure described for 5-13a, but substituting 4-fluorobenzoyl chloride for benzoyl chloride, 5-13d was prepared.

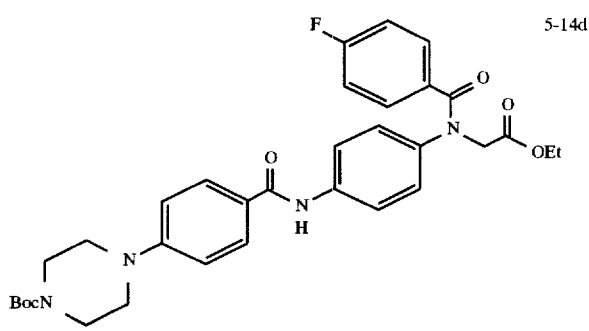

5-14d

Step 2: N-{4-|4-(4-tert-Butyloxycarbonyl-piperazin-1-yl)-phenylcarbonyl-amino|phenyl}-N-4-fluorobenzoylglycine ethyl ester (5-14d)

Following the procedure described for 4-10a, but substituting N-4-nitrophenyl-N-4-fluorobenzoylglycine ethyl ester (5-13d) for N-4-nitrophenyl-N-phenylsulfonylglycine ethyl ester (4-8a), 5-14d was prepared.

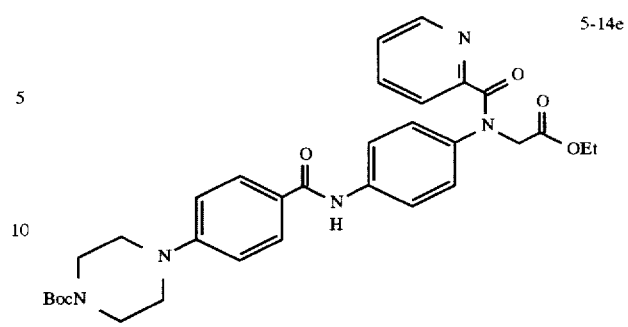

5-14e

Step 2 N-{4-|4-(4-tert-Butyloxycarbonyl-piperazin-1-yl)-phenylcarbonyl-amino|phenyl}-N-picolinoylglycine ethyl ester (5-14e)

Following the procedure described for 4-10a, but substituting N-4-nitrophenyl-N-picolinoyl-glycine ethyl ester (5-13d) for N-4-nitrophenyl-N-phenylsulfonylglycine ethyl ester (4-8a), 5-14e was prepared.

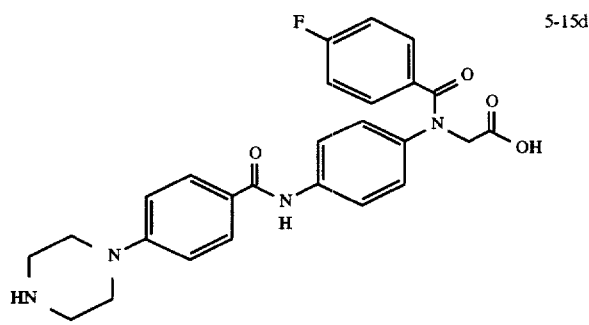

5-15d

Step 3: N-{4-|4-(Piperazin-1-yl)phenylcarbonylamino| phenyl}-N-4-fluoro-benzoylglycine (5-15d)

Following the procedure described for 4-11a, but substituting N-{4-|4-(4-tert-butyloxycarbonyl-piperazin-1-yl)-phenylcarbonylamino|phenyl}-N-4-fluorobenzoyl-glycine ethyl ester (5-14d) for N-{4-|4-(4-tert-butyloxycarbonyl-piperazin-1-yl)-phenylcarbonylamino|phenyl}-N-phenylsulfonylglycine ethyl ester (4-10a), 5-15d was prepared.

Analysis calculated for $C_{26}H_{25}FN_4O_4 \cdot 1.40$ TFA·0.30 $H_2O$ C, 53.92; H, 4.24; N, 8.73 Found: C, 53.90; H, 4.23; N, 8.83

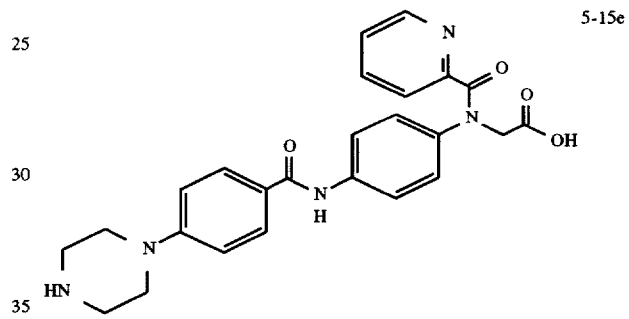

5-15e

Step 3 N-{4-|4-(Piperazin-1-yl)phenylcarbonylamino| phenyl}-N-picolinoyl-glycine (5-15e)

Following the procedure described for 4-11a, but substituting N-{4-|4-(4-tert-butyloxycarbonyl-piperazin-1-yl)-phenylcarbonylamino|phenyl}-N-picolinoylglycine ethyl ester (5-14e) for N-{4-|4-(4-tert-butyloxycarbonyl-piperazin-1-yl)-phenylcarbonylamino|phenyl}-N-phenylsulfonylglycine ethyl ester (4-10a), 5-15e was prepared.

Analysis calculated for $C_{25}H_{25}N_5O_4 \cdot 2.10$ TFA·0.20 $H_2O$ C, 49.92; H, 3.95; N, 9.97 Found: C, 49.88; H, 3.95; N, 10.04

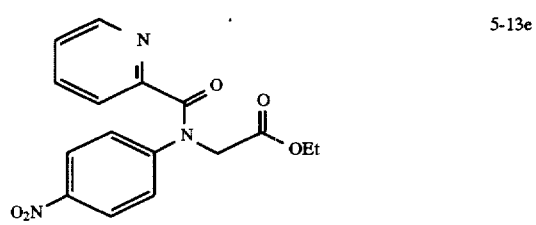

5-13e

Step 1: N-4-Nitrophenyl-N-picolinoyl-glycine ethyl ester (5-13d)

Following the procedure described for 5-13a, but substituting picolinoyl chloride hydrochloride for benzoyl chloride, 5-13d was prepared.

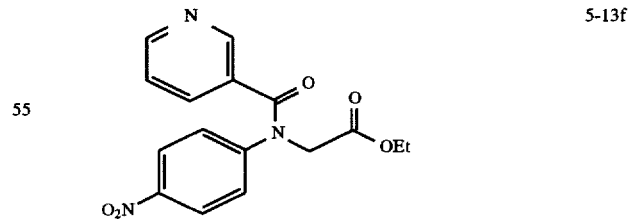

5-13f

Step 1: N-4-Nitrophenyl-N-nicotinoyl-glycine ethyl ester (5-13f)

Following the procedure described for 5-13a, but substituting nicotinoyl chloride hydrochloride for benzoyl chloride, 5-13f was prepared.

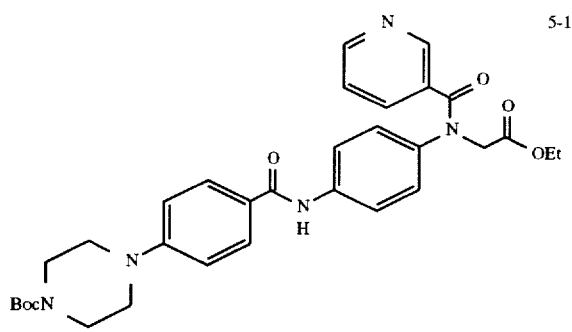

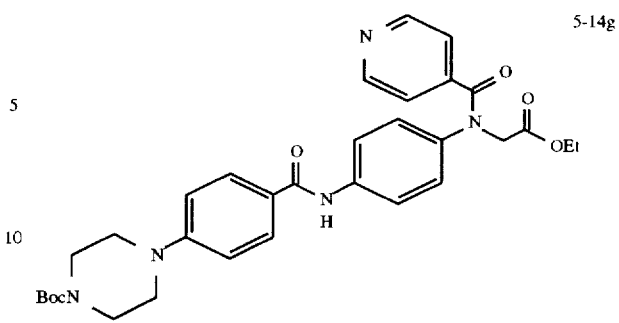

Step 2: N-{4-[4-(4-tert- Butyloxycarbonyl-piperazin-1-yl)-phenylcarbonyl amino|phenyl}-N-nicotinoylglycine ethyl ester (5-14f)

Following the procedure described for 4-10a, but substituting N-4-nitrophenyl-N-picolinoyl-glycine ethyl ester (5-13f) for N4-nitrophenyl-N-phenylsulfonylglycine ethyl ester (4-8a), 5-14f was prepared.

Step 2: N-{4-[4-(4-tert-Butyloxycarbonyl-piperazin-1-yl)-phenylcarbonyl-amino|phenyl}-N-isonicotinoylglycine ethyl ester (5-14g)

Following the procedure described for 4-10a, but substituting N-4-nitrophenyl-N-isonicotinoyl-glycine ethyl ester (5-13g) for N-4-nitrophenyl-N-phenylsulfonylglycine ethyl ester (4-8a), 5-14g was prepared.

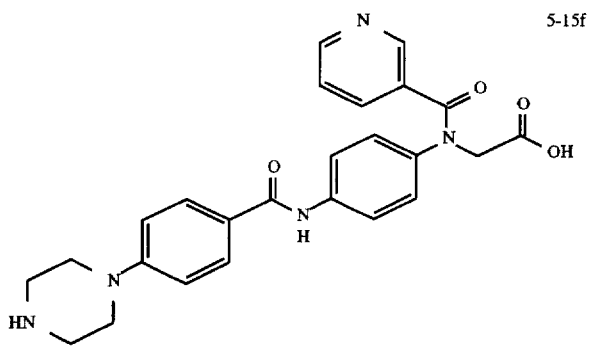

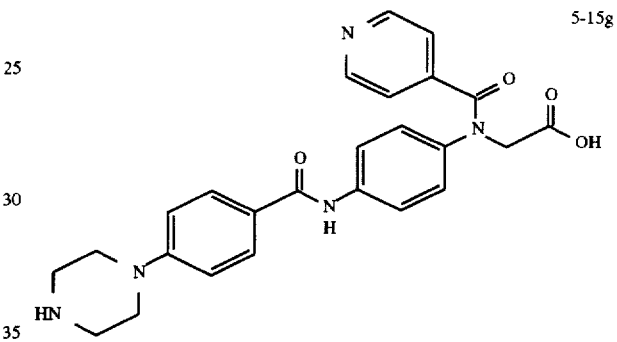

Step 3 N-{4-[4-(Piperazin-1-yl)phenylcarbonylamino| phenyl}-N-nicotinoyl-glycine (5-15f)

Following the procedure described for 4-11a, but substituting N-{4-[4-(4-tert-butyloxycarbonyl-piperazin-1-yl)-phenylcarbonylamino|phenyl}-N-nicotinoylglycine ethyl ester (5-14f) for N-{4-[4-(4-tert-butyloxycarbonyl-piperazin-1-yl)-phenylcarbonyl-amino|phenyl}-N-phenylsulfonylglycine ethyl ester (4-10a), 5-15f was prepared.

Analysis calculated for $C_{25}H_{25}N_5O_4 \cdot 2.20$ TFA.0.35 $H_2O$ C, 49.27; H, 3.92; N, 9.77 Found: C, 49.25; H, 3.92; N, 10.12

Step 3: N-{4-[4-(Piperazin-1-yl)phenylcarbonylamino| phenyl}-N-isonicotinoyl-glycine (5-1 5g)

Following the procedure described for 4-11a, but substituting N-{4-[4-(4-tert-butyloxycarbonyl-piperazin-1-yl) phenylcarbonylamino|phenyl}-N-isonicotinoylglycine ethyl ester (5-1 4g) for N-{4-[4-(4-tert-butyloxycarbonyl-piperazin-1-yl)-phenylcarbonylamino|phenyl}-N-phenylsulfonylglycine ethyl ester (4-10a), 5-15g was prepared.

Analysis calculated for $C_{25}H_{25}N_5O_4 \cdot 2.35$ TFA.0.65 $H_2O$ C, 48.26; H, 3.91; N, 9.47 Found: C, 48.25; H, 3.90; N, 9.57

EXAMPLE 5G

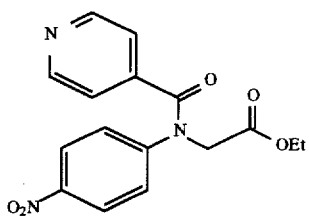

Step 1: N-4-Nitrophenyl-N-isonicotinoyl-glycine ethyl ester (5-13g)

Following the procedure described for 5-13a, but substituting isonicotinoyl chloride hydrochloride for benzoyl chloride, 5-13g was prepared.

EXAMPLE 5H

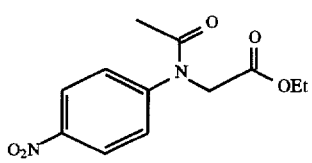

Step 1: N-4-Nitrophenyl-N-acetyl-glycine ethyl ester (5-13h)

Following the procedure described for 5-13a, but substituting acetyl chloride for benzoyl chloride, 5-13h was prepared.

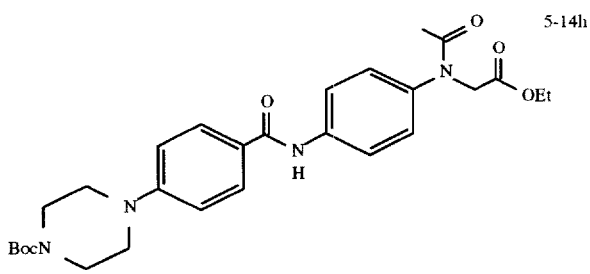

5-14h

Step 2: N-{4-|4-(4-tert-Butyloxycarbonyl-piperazin-1-yl)-phenylcarbonyl-amino|phenyl}-N-acetylglycine ethyl ester (5-14h)

Following the procedure described for 4-10a, but substituting N-4-nitrophenyl-N-acetyl-glycine ethyl ester (5-13h) for N-4-nitrophenyl-N-phenylsulfonylglycine ethyl ester (4-8a), 5-14h was prepared.

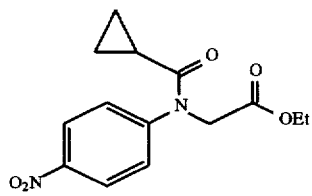

5-15h

Step 3: N-{4-|4-(Piperazin-1-yl)phenylcarbonylamino| phenyl}-N-acetyl-glycine (5-15h)

Following the procedure described for 4-11a, but substituting N-{4-|4-(4-tert-butyloxycarbonyl-piperazin-1-yl)-phenylcarbonylamino|phenyl}-N-acetylglycine ethyl ester (5-14h) for N-{4-|4-(4-tert-butyloxycarbonyl-piperazin-1-yl)-phenylcarbonyl-amino|phenyl}-N-phenylsulfonylglycine ethyl ester (4-10a), 5-15h was prepared.

Analysis calculated for $C_{21}H_{24}N_4O_4 \cdot 1.30$ TFA $\cdot 0.55$ $H_2O$ C, 51.11; H, 4.80; N, 10.10 Found: C, 51.09; H, 4.74; N, 10.25

EXAMPLE 5I

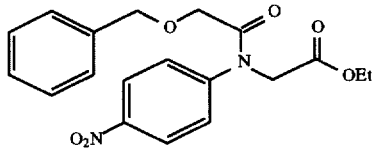

5-13i

Step 1: N-4-Nitrophenyl-N-cyclopropanecarboxylglycine ethyl ester (5-13i)

Following the procedure described for 5-13a, but substituting cyclopropanecarbonyl chloride for benzoyl chloride, 5-13i was prepared.

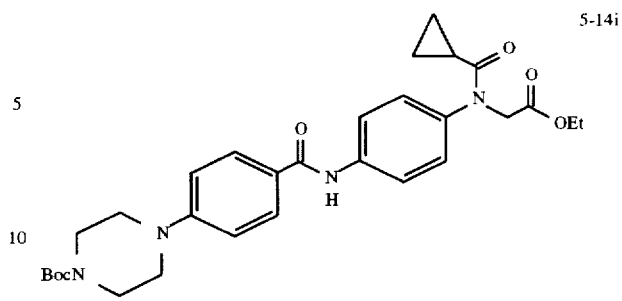

5-14i

Step 2: N-{4-|4-(4-tert-Butyloxycarbonyl-piperazin-1-yl)-phenylcarbonyl-amino|phenyl}-N-cyclopropanecarboxylglycine ethyl ester (5-14i)

Following the procedure described for 4-10a, but substituting N-4-nitrophenyl-N-cyclopropanecarboxylglycine ethyl ester (5-13i) for N-4-nitrophenyl-N-phenylsulfonylglycine ethyl ester (4-8a), 5-14i was prepared.

5-15i

Step 3: N-{4-|4-(Piperazin-1-yl)phenylcarbonylamino| phenyl}-N-cyclopropanecarboxylglycine (5-15i) Following the procedure described for 4-11a, but substituting N-{4-|4-(4-tert-butyloxycarbonyl-piperazin-1-yl)-phenylcarbonylamino|phenyl}-N-cyclopropanecarboxylglycine ethyl ester (5-14i) for N-{4-|4-(4-tert-butyloxycarbonyl-piperazin-1-yl)-phenylcarbonylamino|phenyl}-N-phenylsulfonylglycine ethyl ester (4-10a), 5-15i was prepared.

Analysis calculated for $C_{23}H_{26}N_4O_4 \cdot 1.38$ TFA $\cdot 0.62$ $H_2O$ C, 52.35; H, 4.88; N, 9.48 Found: C, 52.35; H, 4.86; N, 9.65

EXMAPLE 5J 5-13j

Step 1: N-4-Nitrophenyl-N-benzyloxyacetyl-glycine ethyl ester (5-13j)

Following the procedure described for 5-13a, but substituting benzyloxyacetyl chloride for benzoyl chloride, 5-13j was prepared.

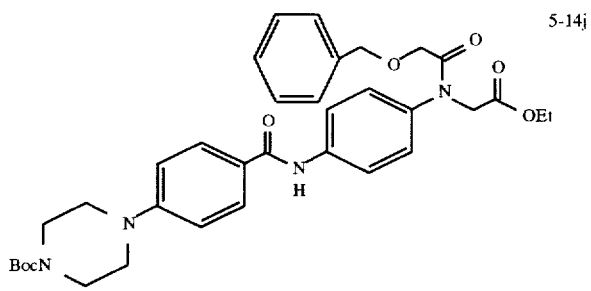

Step 2: N-{4-|4-(4-tert-Butyloxycarbonyl-piperazin-1-yl)-phenylcarbonyl-amino|phenyl}-N-benzyloxyacetylglycine ethyl ester (5-14j)

Following the procedure described for 4-10a, but substituting N-4-nitrophenyl-N-benzyloxyacetylglycine ethyl ester (5-13i) for N-4-nitrophenyl-N-phenylsulfonylglycine ethyl ester (4-8a), 5-14j was prepared.

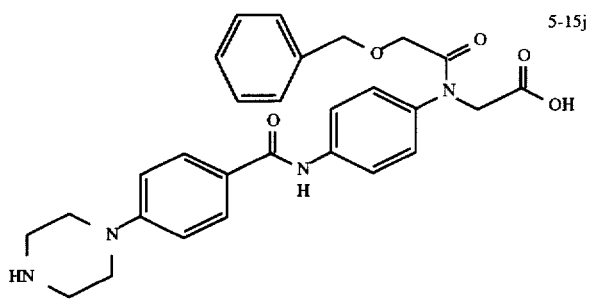

Step 3: N-{4-|4-(Piperazin-1-yl)phenylcarbonylamino|phenyl}-N-benzyloxy-acetylglycine (5-15j)

Following the procedure described for 4-11a, but substituting N-{4-|4-(4-tert-butyloxycarbonyl-piperazin-1-yl)-phenylcarbonylamino|phenyl}-N-benzyloxy-acetylglycine ethyl ester (5-14j) for N-{4-|4-(4-tert-butyloxycarbonyl-piperazin-1-yl)-phenylcarbonylamino|phenyl}-N-phenylsulfonylglycine ethyl ester (4-10a), 5-15j was prepared.

Analysis calculated for $C_{28}H_{30}N_4O_5 \cdot 1.56$ TFA·$0.30$ $H_2O$ C. 54.50; H. 4.73; N. 8.17 found: C. 54.49; H. 4.73; N. 8.51

EXAMPLE 5K

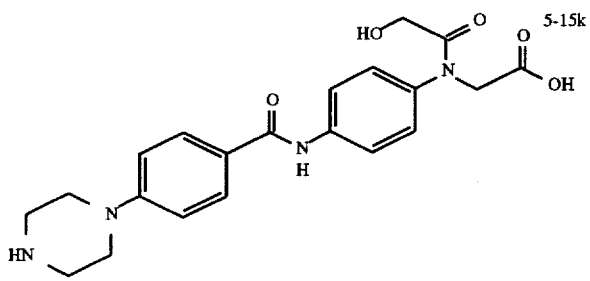

N-{4-|4-(Piperazin-1-yl)phenylcarbonylamino|phenyl}-N-hydroxy-acetylglyciine (5-15k)

A mixture of N-{4-|4-(piperazin-1-yl)phenylcarbonylamino|phenyl}-N-benzyloxyacetylglycine (5-15j, 100 mg), 5% Pd (10 mg) on charcoal, TFA (1 mL) and ethanol (10 mL) was stirred under a balloon of hydrogen gas for 18 h at RT. The resultant mixture was concentrated, and the residue subjected to column chromatography on a reverse phase C-18 column to provide 5-15k.

Analysis calculated for $C_{21}H_{24}N_4O_5 \cdot 1.45$ TFA·$0.40$ $H_2O$ C. 49.07; H. 4.52; N. 9.58 Found: C. 49.08; H. 4.47; N. 9.68

EXAMPLE 5L

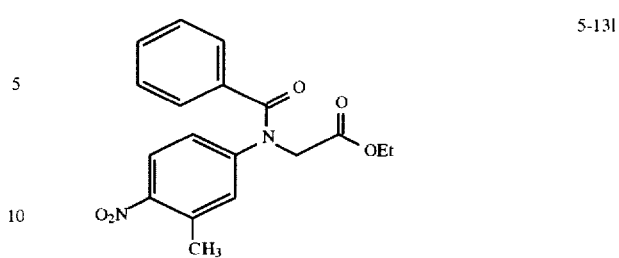

Step 1: N-3-Methyl-4-nitrophenyl-N-benzoyl-glycine ethyl ester (5-13l)

Following the procedure described for 5-13a, but substituting 3-methyl-4-nitroaniline for 4-nitroaniline, 5-13l was prepared.

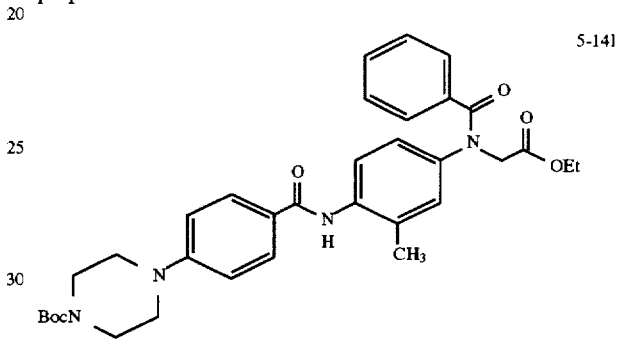

Step 2: N-{4-|4-(4-tert-Butyloxycarbonyl-piperazin-1-yl)-phenylcarbonyl-amino|-3-methyl-phenyl}-N-benzoylglycine ethyl ester (5-14l)

Following the procedure described for 4-10a, but substituting N-3-methyl-4-nitrophenyl-N-benzoyl-glycine ethyl ester (5-13l) for N-4-nitrophenyl-N-phenylsulfonylglycine ethyl ester (4-8a), 5-14l was prepared.

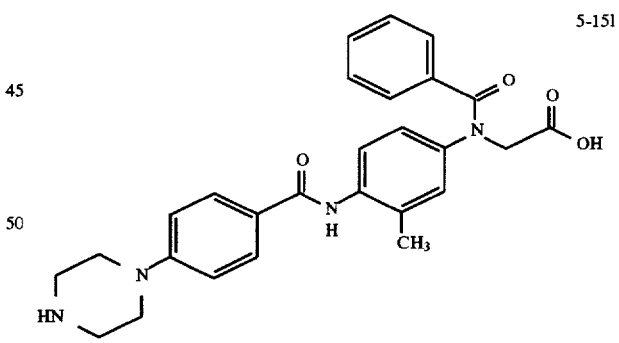

Step 3: N-{4-|4-(Piperazin-1-yl)phenylcarbonylamino|-3-methyl-phenyl}-N-2benzoylglycine (5-15l)

Following the procedure described for 4-11a, but substituting N-{4-|4-(4-tert-butyloxycarbonyl-piperazin-1-yl)-phenylcarbonylamino|-3-methyl-phenyl}-N-benzoylglycine ethyl ester (5-14l) for N-{4-|4-(4-tert-butyloxycarbonyl-piperazin-1-yl)-phenylcarbonylamino|phenyl}-N-phenylsulfonylglycine ethyl ester (4-10a), 5-15l was prepared.

Analysis calculated for $C_{27}H_{28}N_4O_4 \cdot 1.52$ TFA·$0.54$ $H_2O$ C. 55.04; H. 4.70; N. 8.55 found: C. 55.03; H. 4.71; N. 8.84

EXAMPLE 5M

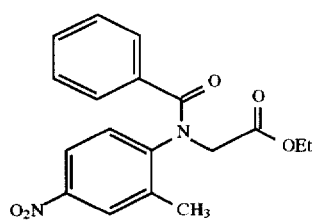
5-13m

Step 1: N-2-Methyl-4-nitrophenyl-N-benzoyl-glycine ethyl ester (5-13m)

Following the procedure described for 5-13a, but substituting 2-methyl-4-nitroaniline for 4-nitroaniline, 5-13m was prepared.

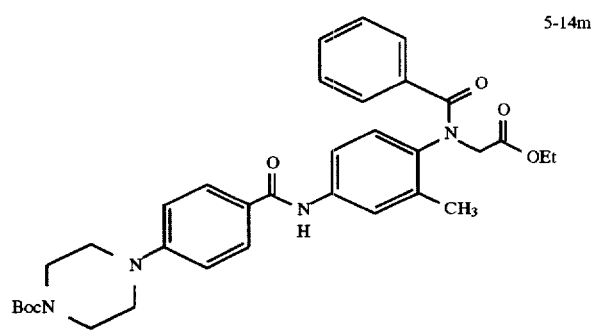
5-14m

Step 2: N-{4-|4-(4-tert-Butyloxycarbonyl-piperazin-1-yl)-phenylcarbonyl-amino|-2-methyl-phenyl}-N-benzoylglycine ethyl ester (5-14m)

Following the procedure described for 4-10a, but substituting N-2-methyl-4-nitrophenyl-N-benzoylglycine ethyl ester (5-13m) for N-4-nitrophenyl-N-phenylsulfonylglycine ethyl ester (-8a), 5-14m was prepared.

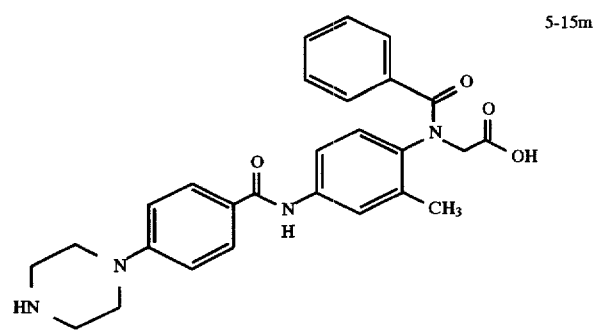
5-15m

Step 3: N-{4-|4-(Piperazin-1-yl)phenylcarbonylamino|-2-methyl-phenyl}-N-2-benzoylglycine (5-15m)

Following the procedure described for 4-11a, but substituting N-{4-|4-(4-tert-butyloxycarbonyl-piperazin-1-yl)-phenylcarbonylamino|-2-methyl-phenyl}-N-benzoylglycine ethyl ester (5-14m) for N-{4-|4-(4-tert-butyloxycarbonyl-piperazin-1-yl)-phenylcarbonylamino|phenyl}-N-phenylsulfonylglycine ethyl ester (4-10a), 5-15m was prepared.

Analysis calculated for $C_{27}H_{23}N_4 \cdot 1.56$ TFA $0.58$ $H_2O$ C, 54.74; H, 4.69; N, 8.48 Found: C, 54.75; H, 4.69; N, 8.74

EXAMPLE 5N

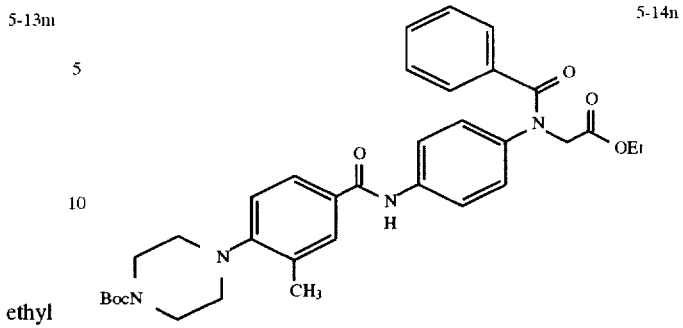
5-14n

Step 1: N-{4-|4-(4-tert-Butyloxycarbonyl-piperazin-1-yl)-3-methylphenyl-carbonylamino|-phenyl}-N-benzoylglycine ethyl ester (5-14n)

Following the procedure described for 4-10a, but substituting N-4-nitrophenyl-N-benzoylglycine ethyl ester (5-13a) for N-4-nitrophenyl-N-phenylsulfonylglycine ethyl ester (4-8a), and substituting 4-|4-(tert-butyloxycarbonyl)piperazin-1-yl|-3-methylbenzoic acid for 4-|4-(tert-butyloxycarbonyl)piperazin-1-yl|-benzoic acid, 5-14n was prepared.

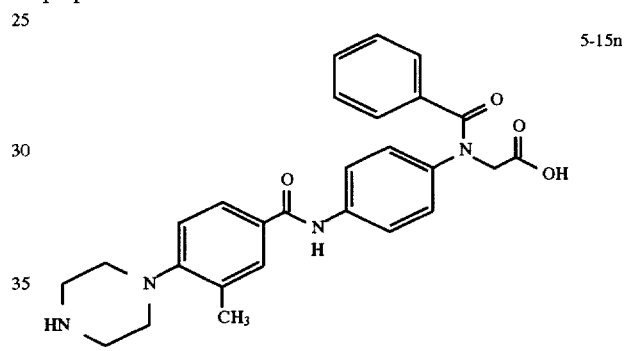
5-15n

Step 2: N-{4-|4-(Piperazin-1-yl)-3-methyl-phenylcarbonylamino|-phenyl}-N-benzoyl glycine (5-15n)

Following the procedure described for 4-11a, but substituting N-{4-|4-(4-tert-butyloxycarbonyl-piperazin-1-yl)-3-methylphenylcarbonylamino|-phenyl}-N-benzoylglycine ethyl ester (5-14n) for N-{4-|4-(4-tert-butyloxycarbonyl-piperazin-1-yl)-phenylcarbonylamino|phenyl}-N-phenylsulfonylglycine ethyl ester (4-10a), 5-15n was prepared.

Analysis calculated for $C_{27}H_{28}N_4)_4 \cdot 1.42$ TFA$\cdot 0.44$ $H_2O$ C, 55.79; H, 4.75; N, 8.72 Found: C, 55.80; H, 4.76; N, 8.78

EXAMPLE 5O

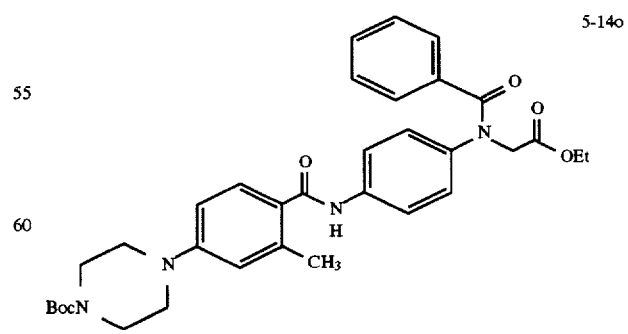
5-14o

Step 1: N-{4-|4-(4-tert-Butyloxycarbonyl-piperazin-1-yl)-2-methylphenyl-carbonylamino|-phenyl}-N-benzoylglycine ethyl ester (5-14o)

Following the procedure described for 4-10a, but substituting N-4-nitrophenyl-N-benzoylglycine ethyl ester (5-13a) for N-4-nitrophenyl-N-phenylsulfonylglycine ethyl ester (4-8a), and substituting 4-[4-(tert-butyloxycarbonyl)piperazin-1-yl]-2-methyl-benzoic acid for 4-[4-(tert-butyloxycarbonyl)piperazin-1-yl]-benzoic acid, 5-14o was prepared.

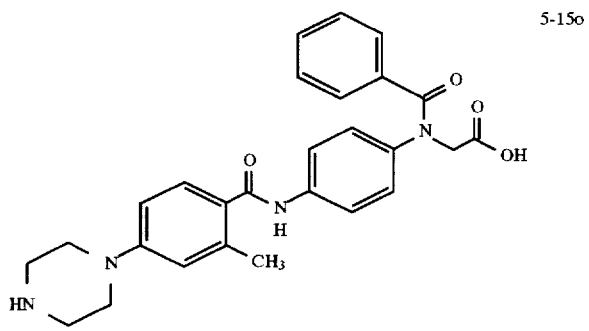

5-15o

Step 2: N-{4-[4-(Piperazin-1-yl)-2-methylphenylcarbonylamino]-phenyl}-N-benzoylglycine (5-15o)

Following the procedure described for 4-11a, but substituting N-{4-[4-(4-tert-butyloxycarbonyl-piperazin-1-yl)-2-methylphenylcarbonylamino]-phenyl}-N-benzoylglycine ethyl ester (5-14o) for N-{4-[4-(4-tert-butyloxycarbonyl-piperazin-1-yl)-phenylcarbonylamino|phenyl}-N-phenylsulfonylglycine ethyl ester (4-10a), 5-15o was prepared.

Analysis calculated for $C_{27}H_{28}N_4O_4 \cdot 1.56$ TFA $\cdot 0.46$ $H_2O$ C, 54.92; H, 4.66; N, 8.51 Found: C, 54.93; H, 4.67; N, 8.58

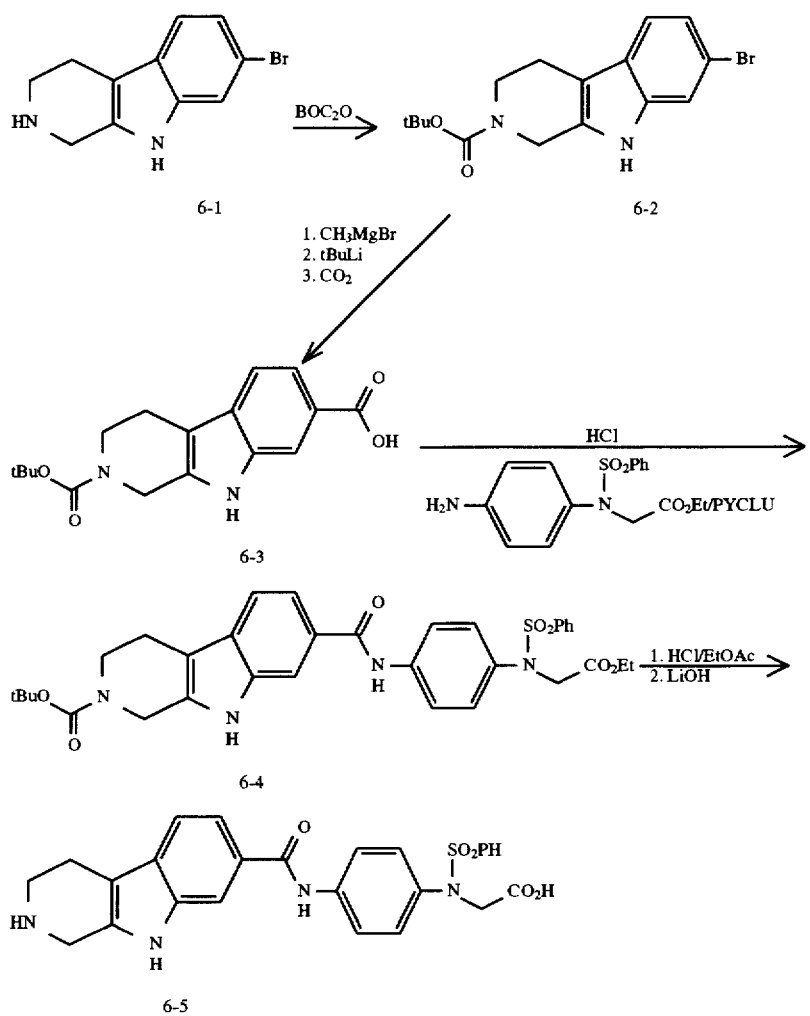

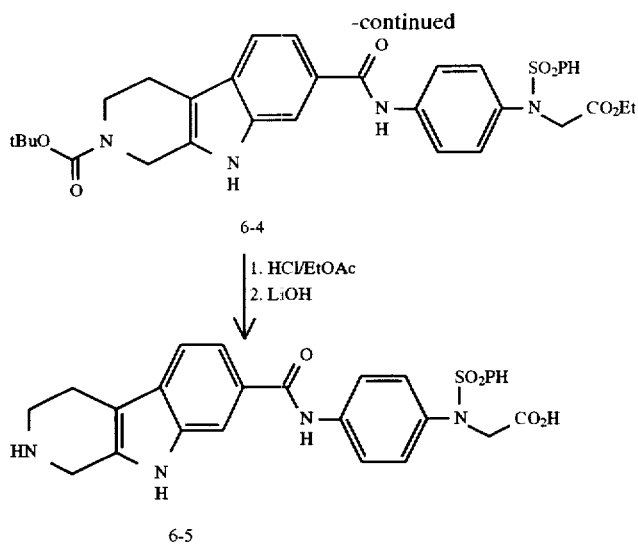

EXAMPLE 6

Step 1: 9-H-2-(1,1-Dimethylethoxycarbonyl)-7-bromo β-carboline (6-2)

A suspension of 6-1, prepared by the method of Rinehart et al., (*JACS*, 1987, 109, p 3378–3387) (0.366 g, 1.46 mmol) in CH$_2$Cl$_2$ (8 mL) was treated with triethylamine (0.61 mL, 4.4 mmol) followed by di-tert-butyldicarbonate (0.38 g, 1.7 mmol) for 1 hour at room temperature. The solution was concentrated and the residue chromatographed (20% EtOAc/Hexanes) to give 6-2 as a white solid. R$_f$(20% EtOAc/Hexanes) 0.28

$^1$H NMR (400 MHz, CDCl$_3$) δ 8.0–7.6 (m, 1H), 7.46 (s, 1H), 7.33 (d, 1H), 7.2 (d, 1H), 4.6 (bs, 2H), 3.78 (bs, 2H), 2.76 (bs, 2H), 1.5 (s, 9H).

Step 2: 9-H-2-(1,1-Dimethylethoxycarbonyl)-β-carbolin-7-yl carboxylic acid (6-3)

A solution of 6-2 (0.26 g, 0.734 mmol) in THF (10 mL) was cooled to 0° C. and treated with methylmagnesium chloride (3.0M in THF, 0.29 mL, 0.87 mmol) to give a pale yellow solution. After 15 minutes the solution was cooled to −78° C. and treated with t-BuLi (1.7M in pentane, 4.35 mL, 7.39 mmol) to give a bright yellow solution. After 10 minutes CO$_2$ gas was bubbled vigorously through the solution for 10 minutes. Saturated NH$_4$Cl, water and enough 6N NaOH to reach pH12 were added and the solution extracted with EtOAc. The EtOAc layer was back extracted with 0.5 NaOH and the aqueous layers combined, acidified to pH 7 and extracted with EtOAc, the EtOAc layer was dried (Na$_2$SO$_4$) filtered and concentrated to give 6-3 as an off-white solid.

R$_f$(75:25:1 CHCl$_3$/MeOH/HOAc)0.48.

$^1$H NMR (400 MHz, DMSO-d$_6$) δ 12.0 (bs, 1H), 11.2 (s, 1H), 7.93 (s, 1H), 7.6 (d, 1H), 7.45 (d, 1H), 4.6 (s, 2H), 3.68 (m, 2H), 2.7 (m, 2H), 1.4 (s, 9H).

Step 3: N-{4-[9-Boc-β-carboline-7-yl)carbonylamino] phenyl}-N-phenyl-sulfonyl glycine (6-4)

A solution of 6-3 (0.075 g, 0.24 mmol) and N-4-aminophenyl-N-phenylsulfonylglycine ethyl ester (0.086 g, 0.28 mmol) in CH$_2$Cl$_2$ (3 mL) was treated with diisopropylamine and PYCLU to give 6-4 as a white solid after chromatography in a gradient of 40 to 50% EtOAc/Hexanes.

R$_f$(40% EtOAc/Hexanes)0.13

$^1$H NMR (400 MHz, CDCl$_3$) δ 8.5–8.2 (m, 1H), 8.0 (d, 1H), 7.2 (2s, 2H), 7.6 (2s, 2H), 7.58 (m, 1H), 7.53 (s, 2H), 7.47 (m, 2H), 7.2 (d, 2H), 4.68 (bs, 2H), 4.4 (s, 2H), 4.13 (q, 2H), 3.8 (bs, 2H), 2.7 (bs, 2H), 1.5 (s, 9H), 1.2 (t, 3H).

Step 4: N-{4-[(9-H-β-Carboline-7-yl)carbonylamino] phenyl}-N-phenyl-sulfonyl glycine (6-5)

A solution of 6-4 (0.088 g, 0.139 mmol) in EtOAc (15 mL) was treated first with HCl gas, then with LiOH.H$_2$O to give 6-5 as a white solid after chromatography in 18:1:1 EtOH/H$_2$O/NH$_4$OH.

R$_f$(18:1:1 EtOH/H$_2$O/NH$_4$OH) 0.43

$^1$H NMR (400 MHz, D$_2$O) δ 7.79 (s, 1H), 7.6 (m, 1H), 7.52 (m, 2H), 7.46 (m, 4H), 7.32 (d, 2H), 7.08 (d, 2H), 4.08 (s, 2H), 3.84 (s, 2H), 2.95 (m, 2H), 2.63 (m, 2H).

SCHEME 7

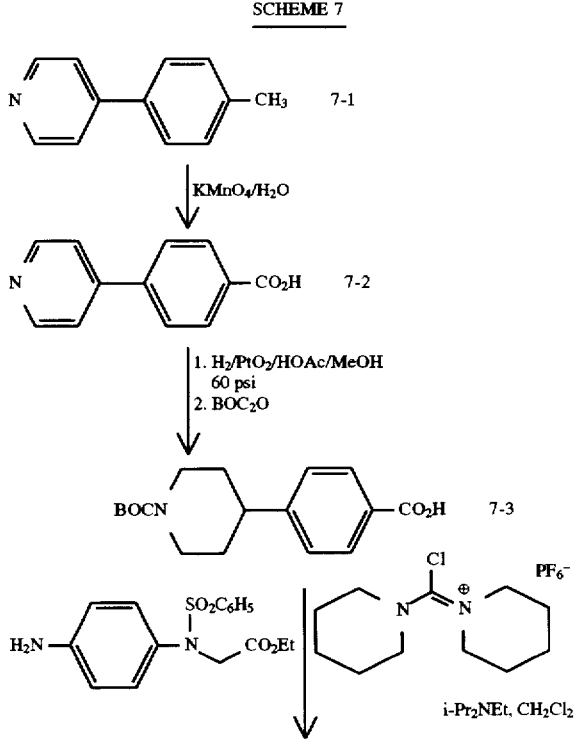

-continued
SCHEME 7

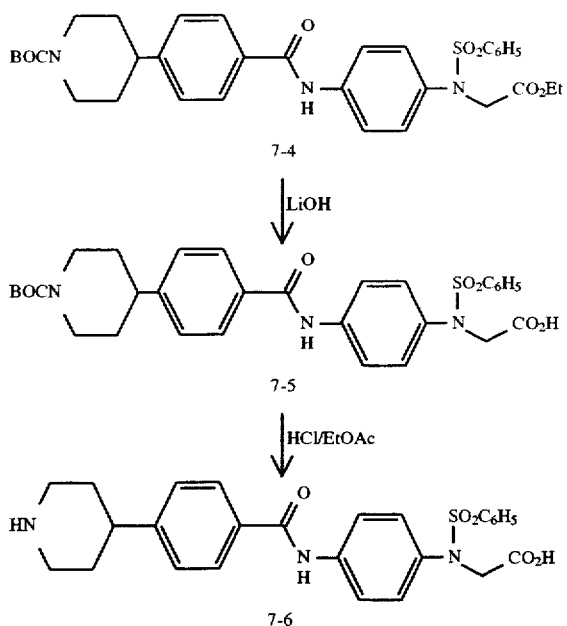

EXAMPLE 7

Step 1: 4-(4-Pyridyl)phenylcarboxylate (7-2)

A slurry of 7-1 (5 g, 29.6 mmol, prepared as described in Chambron, J. C.; Sauvage, J. P., Tetrahedron, 1987, 895 and Comins, D. L.; Abdullah, A. H., J. Org. Chem., 1982, 47, 4315 method B) in 200 mL $H_2O$ was treated with 10% HCl until the solids dissolved. The solution was treated with solid $KMnO_4$ in portions (11.2 g, 888 mmol), stirred until the $KMnO_4$ had dissolved and heated to 90° C. for 18 hr. An additional 2 g of $KMnO_4$ was added and the reaction was again heated to 90° C. for 2 hr. The reaction was cooled to ~60° C., filtered and the solids were washed with warm water. The filtrate was evaporated and the residue chromatographed (Silica gel, 10:1:1 $EtOH/H_2O/NH_4OH$) to give 7-2 as an off-white solid.

$^1$H NMR (400 MHz, DMSO) δ 8.61 (m, 2H), 8.0 (m, 2H), 7.72 (m, 4H).

Step 2: 4-(4-N-BOC-piperidinyl)phenylcarboxylate (7-3)

A solution of 7-2 (0.5 g, 2.5 mmol) in 20 mL 20% HOAc/MeOH was treated with 250 mg $PtO_2$ and hydrogenated at 50 psi for 4 hr. The solution was filtered through Solka Floc, evaporated and azeotroped with heptane to remove excess HOAc. The intermediate amino acid acetic acid salt was obtained as a white solid.

$R_f$(10:1:1 $EtOH/H_2O/NH_4OH$) 0.3.

$^1$H NMR (400 MHz, $CD_3OD$) δ 8.96 (m, 2H), 7.35 (m, 2H), 3.5 (bd, 2H), 3.4 (m, 2H), 3.2 (m, 2H), 3.0 (m, 2H).

A slurry of the amino acid (0.5 g, 1.9 mmol) in 30% $H_2O$/dioxane (12 mL) was treated with 1N NaOH (4.8 mL) and di-tert-butyldicarbonate (0.564 g, 2.58 mmol) at room temperature for 6 hr. The reaction was acidified to pH 5 with 10% $KHSO_4$ and extracted several times with EtOAc.

The EtOAc layers were combined and evaporated to give 7-3 as a white solid.

$R_f$(97:3:1 $CHCl_3/MeOH/HOAc$) 0.39.

$^1$H NMR (400 MHz, $CD_3OD$) δ 7.95 (d, 2H), 7.33 (d, 2H), 4.2 (bd, 2H), 2.85 (b, 3H), 1.8 (bd, 2H), 1.6 (m, 2H), 1.48 (s, 9H).

Step 3: Ethyl 2-(1-phenylsulfonamido-4-(4-(N-(1,1-dimethylethoxycarbonyl)-piperidin-4-yl)phenyl-carboxamide)-phenyl)acetate (7-4)

A solution of 7-3 (0.457 g, 1.5 mmol) N-4-aminophenyl-N-phenylsulfonylglycine ethyl ester (0.50 g, 1.5 mmol) in $CH_2Cl_2$ (10 mL) was treated with diisopropylamine (0.287 mL, 1.65 mmol) and PYCLU (0.594 g, 1.65 mmol) and stirred at room temperature for 24 hours. The solution was diluted with EtOAc and washed with $H_2O$, 10% citric acid, saturated $NaHCO_3$ and brine, dried over $MgSO_4$, filtered and evaporated to give 7-4 as a tan oil. $R_f$(50% EtOAc/Hexanes)0.16

$^1$H NMR (400 MHz, $CDCl_3$) δ 7.8 (d, 1H), 7.7 (d, 1H), 7.58 (m, 3H), 7.45 (m, 2H), 7.32 (d, 1H), 7.2 (d, 1H), 4.4 (s, 2H), 4.25 (m, 2H), 4.15 (q, 2H), 2.82 (m, 2H), 2.78 (m, 1H), 1.82 (bd, 2H), 1.6 (m, 3H), 1.45 (s, 9H), 1.2 (t, 3H).

Step 4: N-{4-|4-N-Boc-piperidin-4-yl)phenylcarboxylamino|-phenyl}-N-phenylsulfonylglycine (7-5)

A solution of 7-4 (0.7 g, 1.12 mmol) in 1:1:1 MeOH/$H_2O$/THF was treated with $LiOH.H_2O$ (0.097 g, 1.12 mmol) for 24 hours. The solution was diluted with EtOAc and 10% $KHSO_4$ and the layers separated. The organic layer was dried over $MgSO_4$, filtered and evaporated to give 7-5 as a tan solid.

$R_f$(9:1:1 $CH_2Cl_2/MeOH/HOAc$)0.55

$^1$H NMR (400 MHz, $CD_3OD$) δ 7.89 (m, 2H), 7.65 (m, 5H), 7.05 (m, 2H), 7.8 (d, 2H), 7.18 (d, 2H), 4.4 (s, 2H), 4.2 (bd, 2H), 2.85 (m, 3H), 2.83 (bd, 2H), 1.6 (m, 1H), 1.48 (s, 9H).

Step 5: N-{4-|4-Piperidin-4-yl)phenylcarbonylamino|phenyl}-N-phenyl-sulfonylglycine (7-6)

A solution of 7-5 (0.4 g, 0.67 mmol) in EtOAc (5 mL) was cooled to -78° C., saturated with HCl gas, warmed to 0° C. and stirred for 1 hour, then concentrated at ambient temperature to give 7-6 as a white solid after chromatography in 10:1:1 $EtOH/H_2O/NH_4OH$.

$R_f$(10:1:1 $EtOH/H_2O/NH_4OH$)0.34

$^1$H NMR (400 MHz, $D_2O$+NaOD) δ 7.65-7.4 (m, 7H), 7.35 (d, 2H), 7.26 (m, 2H), 7.05 (m, 2H), 4.08 (bs, 2H), 2.95 (m, 2H), 2.55 (m, 3H), 1.65 (m, 2H), 1.45 (m, 2H).

SCHEME 8

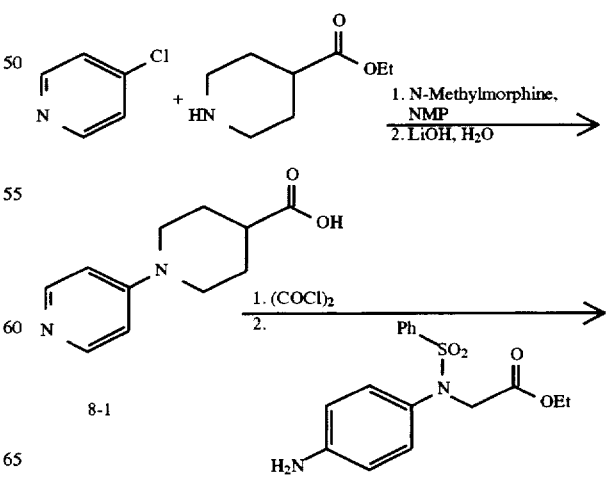

SCHEME 8 -continued

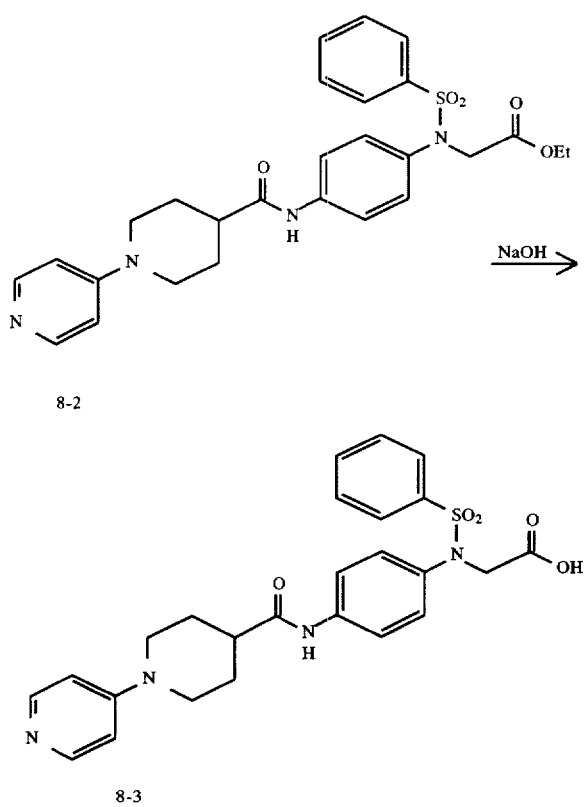

EXAMPLE 8

Step 1: 4-(Pyridyl)piperidin-4-yl-carboxylic acid (8-1)

Ethyl isonipecotate (6.0 g, 38.66 mmol), 4-chloropyridine hydrochloride (5.9 g, 38.66 mmol) and N-methylmorpholine (9.3 mL, 85.0 mmol) were dissolved in N-methylpyrrolidinone (50 μL) and the resulting solution heated at 100° for 48 h. The solution was concentrated in vacuo and the residue dissolved in ethyl acetate (200 mL) and washed with water and brine (2×100 mL), then dried ($Na_2SO_4$) and evaporated. The resulting residue was purified by flash chromatography (5%MeOH/$CH_2Cl_2$) to afford ethyl 4-(pyridyl)piperidin-4-yl-carboxylate as a crystalline solid.

A solution of the above ester (10 g, 42.7 mmol) in THF (50 mL) was treated with 1N LiOH (47 mL, 47.0 mmol) and $H_2O$ (50 mL). The resulting solution was concentrated and the aqueous residue cooled to 0° C., then adjusted to pH≈6 with 1N HCl and the resulting solid 8-1, collected by filtration.

Step 2: N-{4-[N-(4-Pyridyl)-piperidinyl-4-carbonylamino] phenyl}-N-phenyl-sulfonyl-glycine methyl ester (8-2)

Following the procedure described for 4-10a, but substituting N-(4-pyridyl)-piperidinyl-4-carboxylic acid (8-1) for 4-[4-(tert-butyloxycarbonyl)-piperazin-1-yl]benzoic acid, 8-2 was prepared.

Step 3: N-{4-[N-(4-Pyridyl)-piperidinyl-4-carbonylamino] phenyl}-N-phenylsulfonyl-glycine (8-3)

Following the procedure described for 4-11a, N-{4-[N-(4-pyridyl)-piperidinyl-4-carbonylamino]phenyl}-N-phenylsulfonylglycine methyl ester 8-2 was hydrolyzed. HPLC purification provided 8-3.

Analysis calculated for $C_{25}H_{25}N_4O_5S.1.40$ TFA.0.80 $H_2O$ C, 50.02; H, 4.23; N, 8.39 Found: C, 50.00; H, 4.24; N, 8.65

SCHEME 9

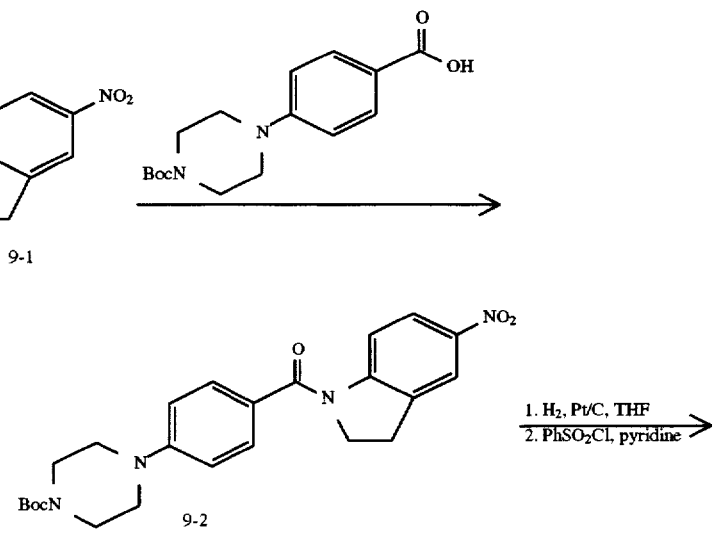

-continued
SCHEME 9

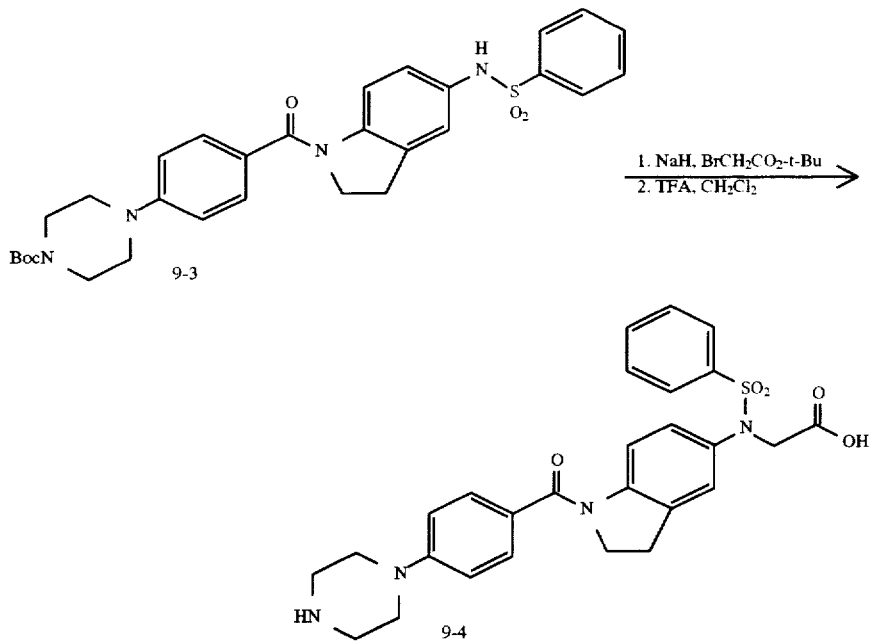

EXAMPLE 9

Step 1: N-4-(4-tert-Butyloxycarbonylpiperaziny-1-y)-benzoyl|-5-nitro-indoline (9-2)

Following the procedure described for 4-10a, but substituting 5-nitroindoline (2-1) for N-4-aminophenyl-N-phenylsulfonylglycine ethyl ester, 9-2 was prepared.

Step 2: N-|4-(4-tert-Butyloxycarbonylpiperaziny-1-y)-benzoyl|-5-phenyl-sulfonylamino-indoline (9-3)

Following the procedure described for 3-5a, but subtituting N-|4-(4-tert-butyloxycarbonylpiperaziny-1-y)-benzoyl|-5-nitro-indoline (9-2) for nitrobenzene 3-4, 9-3 was prepared. The catalytic hydrogenation was carried out in the presence of Pt/C in THF.

Step 3: N-{N-|4-(4-tert-Butyloxycarbonylpiperaziny-1-yl)-benzoyl|-5-indolinyl}-N-phenylsufonyl-glycine (9-4)

Following the procedure described for 3-6a, but substituting N-|4-(4-tert-butyloxycarbonylpiperaziny-1-y)-benzoyl|-5-phenylsulfonylamino-indoline (9-3-) for sulfonamide 3-5a, 9-4 was prepared.

Analysis calculated for $C_{27}H_{28}N_4O_5S \cdot 1.50$ TFA C, 52.10; H, 4.30; N, 8.10 Found: C, 52.13; H, 4.26; N, 8.23

SCHEME 10

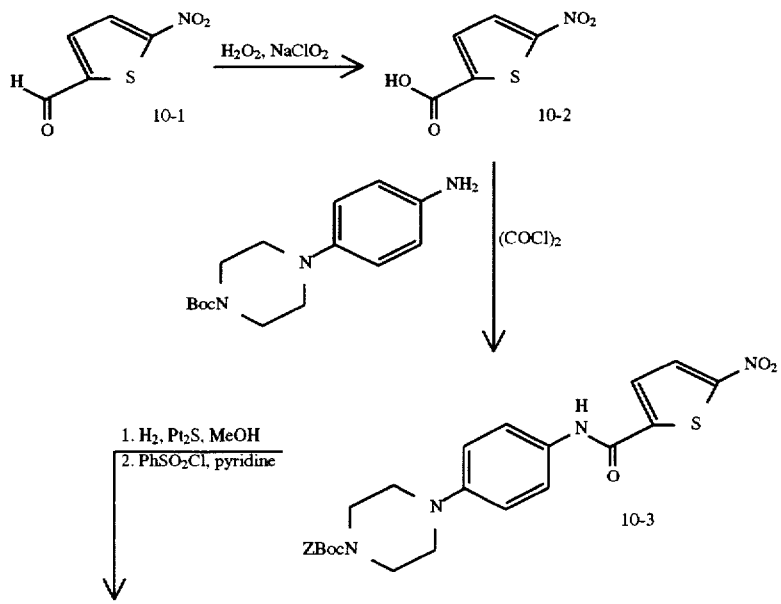

-continued
SCHEME 10

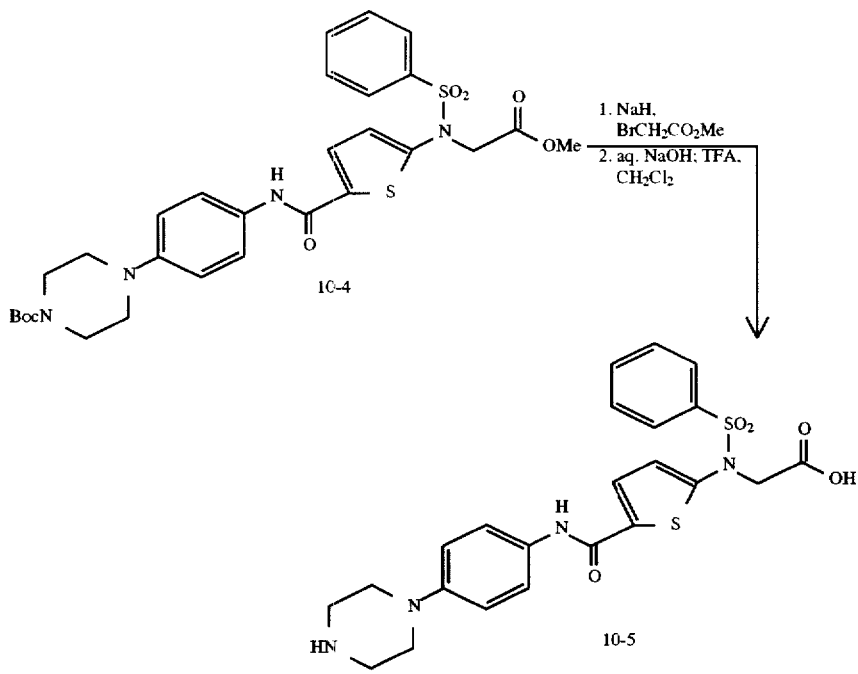

EXAMPLE 10

Step 1: 5-Nitro-thiophene-2-carboxylic acid (10-2)

To a cold (0° C.) mixture of 5-nitro-thiophene-2-carboxaldehyde (10-1) (7.86 g, 50 mmol), $NaH_2PO_4$ (1.86 g, dissolved in 20 mL water), 30% $H_2O_2$ (6 mL) in acetonitrile (50 mL), a solution of $NaClO_2$ (8 g) in water (70 mL) was added over a period of 1 h. After stirring at RT for 5 h, the reaction mixture was treated with sodium sulfite (500 mg) and 1M aq. HCl. The resultant mixture was extracted with ethyl acetate (3×). The organic extracts were combined, washed with brine, dried over anhdrous magnesium sulfate, filtered, and concentrated under vacuum to provide acid 10-2.

Step 2: N-(5-Nitro-thiophene-2-carboxyl)-4-(4-tert-butyloxycarbonyl-piperaziny-1-yl)-aniline (10-3)

Following the procedure described for 3-4, but substituting 5-nitro-thiophene-2-carboxylic acid (10-2) for 4-nitrobenzoic acid, 10-3 was prepared.

Step 3: N-{2-[4-(4-tert-Butyloxycarbonylpiperazin-yl)-phenylamino-carbonyl]thien-5-yl}-N-phenylsulfonyl-glycine methyl ester (10-4)

Following the procedure described for 3-5a, but substituting N-(5-nitro-thiophene-2-carboxyl)-4-(4-tert-butyloxycarbonylpiperaziny-1-yl)-aniline (10-3) for 3-4. The reduction was carried out in methanol in the presence of $Pt_2S$ for three hour under a balloon of hydrogen gas. Phenylsulfonylation, was described for 3-5a provided 10-4.

Step 4: N-{2-[4-(1-Piperazin-yl)-phenylaminocarbonyl] thien-5-yl}-N-phenyl-sulfonyl-glycine (10-5)

Following the procedure described for 3-6a, but substituting 10-4 for 3-5a, 10-5 was prepared.

Analysis calculated for $C_{23}H_{24}N_4O_5S_2 \cdot 1.72$ TFA$\cdot 0.28$ $H_2O$ C, 45.25; H, 3.77; N, 7.98 found: C, 45.25; H, 3.77; N, 8.13

SCHEME 11

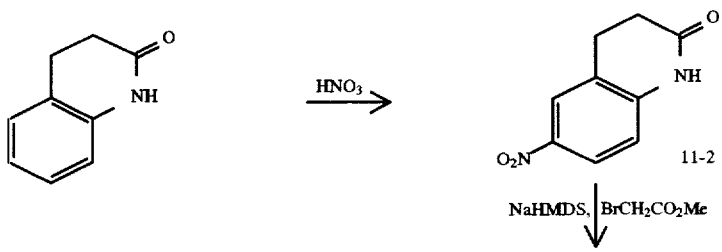

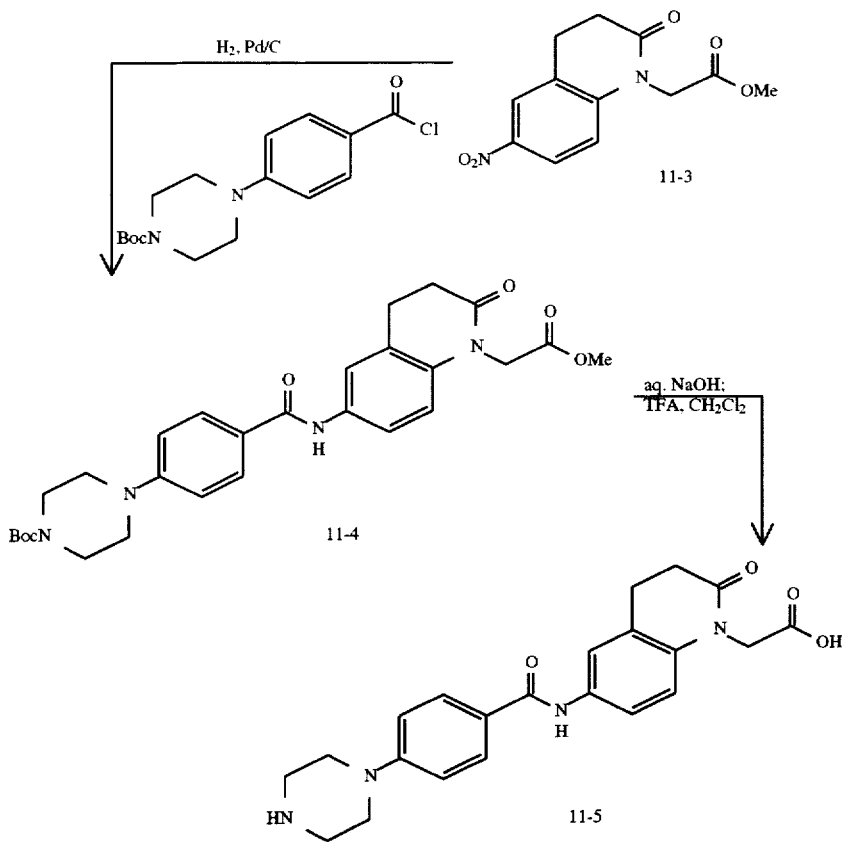

EXAMPLE 11

Step 1: 6-Nitro-3,4-dihydroquinolin-2-(1H)-one (11-2)

To a solution of 3,4-dihydroquinolin-2-(1H)-one (1.50 g) in 78% sulfuric acid (300 mL) at RT, a mixture of 69% nitric acid (0.84 mL) in 78% sulfuric acid (60 mL) was added. The reacting mixture was stirred at RT for 15 min, poured into ice-water, and extracted with methylene chloride (3×200 mL). The organic extracts were combined, washed with brine (4×), dried over anhydrous magnesium sulfate, filtered and concentrated onto silica gel. The residue was loaded onto a column of silica gel, and eluted with 3% methanol in chloroform. Collection and concentration of appropriate fractions provided the nitroquinolinone 11-2.

Step 2: 6-Nitro-1-carbomethoxymethyl-3,4-dihydroquinolin-2-(1H)-one (11-3)

Following the procedure described for 5-13a, but substituting 6-nitro-3,4-dihydroquinolin-2-(1H)-one (11-2) for 4-nitro-N-benzoylaniline, 11-3 was prepared.

Step 3: 6-[4-(4-tert-Butyloxycarbonyl-piperazin-1-yl)-phenylcarbonylamino]-1-carbomethoxymethyl-3,4-dihydroquinolin-2-(1H)-one (11-4)

Following the procedure described for 4-10a, but substituting 6-nitro-1-carbomethoxymethyl-3,4-dihydroquinolin-2-(1H)-one (11-3) for N-4-nitrophenyl-N-phenylsulfonyl-glycine ethyl ester (4-8a), 11-4 was prepared.

Step 4: 6-[4-(4-Piperazin-1-yl)-phenylcarbonylamino]-1-carbohydroxymethyl-3,4-dihydroquinolin-2-(1H)-one (11-5)

Following the procedure described for 4-11 a, but substituting 6-[4-(4-tert-butyloxycarbonyl-piperazin-1-yl)-phenylcarbonylamino]-1-carbomethoxy-methyl-3,4-dihydroquinolin-2-(1H)-one (11-4) for 4-10a, 11-5 was prepared.

Analysis calculated for $C_{22}H_{24}N_4O_4 \cdot 1.22$ TFA $\cdot 0.84$ $H_2O$ C, 52.17; H, 4.82; N, 9.96 Found: C, 52.15; H, 4.82; N, 10.13

EXAMPLE 12

Tablet Preparation

Tablets containing 25.0, 50.0, and 100.0 mg., respectively, of the active compound p) from Table I are prepared as illustrated below:

| TABLE FOR DOSES CONTAINING FROM 25–100 MG OF THE ACTIVE COMPOUND | | | |
|---|---|---|---|
| | Amount-mg | | |
| Active Compound | 25.0 | 50.0 | 100.0 |
| Microcrystalline cellulose | 37.25 | 100.0 | 200.0 |
| Modified food corn starch | 37.25 | 4.25 | 8.5 |
| Magnesium stearate | 0.50 | 0.75 | 1.5 |

All of the active compound, cellulose, and a portion of the corn starch are mixed and granulated to 10% corn starch paste. The resulting granulation is sieved, dried and blended with the remainder of the corn starch and the magnesium stearate. The resulting granulation is then compressed into tablets containing 25.0, 50.0, and 100.0 mg, respectively, of active ingredient per tablet.

EXAMPLE 13

Intravenous formulations

An intravenous dosage form of the above-indicated active compound is prepared as follows:

| Active Compound | 0.5–10.0 mg |
|---|---|
| Sodium Citrate | 5–50 mg |
| Citric Acid | 1–15 mg |
| Sodium Chloride | 1–8 mg |
| Water for Injection (USP) | q.s. to 1 L |

Utilizing the above quantities, the active compound is dissolved at room temperature in a previously prepared solution of sodium chloride, citric acid, and sodium citrate in Water for Injection (USP, see page 1636 of United States Pharmacopeia/National Formulary for 1995, published by United States Pharmacopeial Convention, Inc., Rockville, Md., copyright 1994.

Therapeutic Treatment

Compounds of the invention may be administered to patients where inhibition of human or mammalian platelet aggregation or adhesion is desired.

Compounds of the invention are useful in inhibiting platelet aggregation and thus, they may find utility in surgery on peripheral arteries (arterial grafts, carotid endaterectomy) and in cardiovascular surgery where manipulation of arteries and organs, and/or the interation of platelets with artificial surfaces, leads to platelet aggregation and consumption. The aggregated platelets may form thrombi and thromboemboli. Compounds of the invention may be administered to these surgical patients to prevent the formation of thrombi and thromboemboli.

What is claimed is:

1. The compound having the formula VII wherein X-A, Y, Z and n are defined as follows:

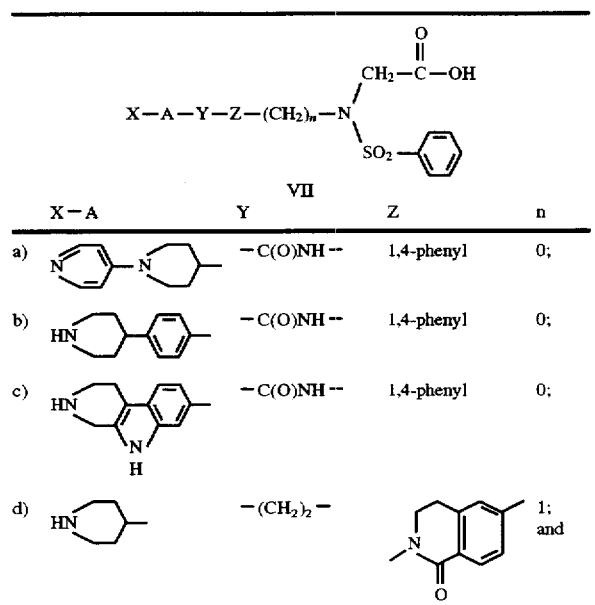

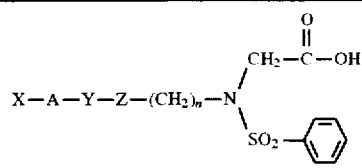

| X–A | Y | Z | n |
|---|---|---|---|
| e) HN⟨⟩- | | –(CH₂)₃–O– | 1,4-phenyl | 1. |

2. A composition for inhibiting the binding of fibrinogen to blood platelets in a mammal, comprising a therapeutically effective amount of a compound of claim 1 and a pharmaceutically acceptable carrier.

3. A composition for inhibiting the aggregation of blood platelets in a mammal, by blocking fibrinogen from acting at its receptor site, comprising a therapeutically effective amount of a compound of claim 1 and a pharmaceutically acceptable carrier.

4. A composition for inhibiting the aggregation of blood platelets in a mammal, by blocking fibrinogen from acting at its receptor site, comprising a therapeutically effective amount of a compound of claim 1 in combination with a thrombolytic agent and a pharmaceutically acceptable carrier.

5. A composition for inhibiting the aggregation of blood platelets in a mammal, by blocking fibrinogen from acting at its receptor site, comprising a therapeutically effective amount of a compound of claim 1 in combination with an anticoagulant agent and pharmaceutically acceptable carrier.

6. A method for inhibiting the binding of fibrinogen to blood platelets in a mammal, comprising treating the mammal with a composition of claim 2.

7. A method for inhibiting the aggregation of blood platelets in a mammal, by blocking fibrinogen from acting at its receptor site, comprising treating the mammal with a composition of claim 3.

8. A method for inhibiting the aggregation of blood platelets in a mammal, by blocking fibrinogen from acting at its receptor site, comprising treating the mammal with a composition of claim 4.

9. A method for inhibiting the aggregation of blood platelets in a mammal, by blocking fibrinogen from acting at its receptor site, comprising treating the mammal with a composition of claim 5.

10. A composition for inhibiting the aggregation of blood platelets in a mammal, by blocking fibrinogen from acting at its receptor site, comprising a a pharmaceutically acceptable carrier and a therapeutically effective amount of a compound of claim 1 in combination with a therapeutically effective amount of two or more agents selected from a thrombolytic agent, an anticoagulant agent, and an antiplatelet agent.

11. A method for inhibiting the aggregation of blood platelets in a mammal, by blocking fibrinogen from acting at its receptor site, comprising treating the mammal with the composition of claim 10.

* * * * *